US012806239B2

(12) United States Patent
Junghans

(10) Patent No.: US 12,806,239 B2
(45) Date of Patent: Nov. 24, 2026

(54) HYDROXYETHYCELLULOSE GEL COMPOSITION COMPRISING BACTERIOPHAGES

(71) Applicant: PhaTEC GmbH, Kiel (DE)

(72) Inventor: Simon Frank Junghans, Kiel (DE)

(73) Assignee: PhaTEC GmbH, Kiel (DE)

( * ) Notice: Subject to any disclaimer, the term of this patent is extended or adjusted under 35 U.S.C. 154(b) by 344 days.

(21) Appl. No.: 18/349,058

(22) Filed: Jul. 7, 2023

(65) Prior Publication Data

US 2024/0156730 A1 May 16, 2024

(30) Foreign Application Priority Data

Jul. 8, 2022 (EP) .................................... 22183895

(51) Int. Cl.
*A61K 35/76* (2015.01)
*A61K 9/06* (2006.01)
*A61K 47/38* (2006.01)
*A61L 26/00* (2006.01)
*A61P 31/04* (2006.01)

(52) U.S. Cl.
CPC ................ *A61K 35/76* (2013.01); *A61K 9/06* (2013.01); *A61K 47/38* (2013.01); *A61L 26/008* (2013.01); *A61P 31/04* (2018.01)

(58) Field of Classification Search
None
See application file for complete search history.

(56) References Cited

U.S. PATENT DOCUMENTS

| | | | |
|---|---|---|---|
| 2010/0291041 A1 | 11/2010 | Dahlen et al. | |
| 2017/0097353 A1 | 4/2017 | Weiss et al. | |
| 2017/0157186 A1* | 6/2017 | Shiach | A61K 9/0014 |
| 2023/0346861 A1 | 11/2023 | Ousterout et al. | |

FOREIGN PATENT DOCUMENTS

| | | | | |
|---|---|---|---|---|
| CN | 1642561 A | 7/2005 | | |
| EP | 2990028 A1 | 3/2016 | | |
| RU | 2754828 C1 | 9/2021 | | |
| SK | 500172020 A3 * | 9/2021 | | |
| WO | 2003000274 A2 | 1/2003 | | |
| WO | 2003010316 A1 | 2/2003 | | |
| WO | 2003077953 A2 | 9/2003 | | |
| WO | 2004091505 A2 | 10/2004 | | |
| WO | 2005023176 A2 | 3/2005 | | |
| WO | 2009037264 A2 | 3/2009 | | |
| WO | 2009090082 A2 | 7/2009 | | |
| WO | 2011005756 A1 | 1/2011 | | |
| WO | 2011154007 A1 | 12/2011 | | |
| WO | 2014078911 A1 | 5/2014 | | |
| WO | 2017047089 A1 | 3/2017 | | |
| WO | 2017108935 A1 | 6/2017 | | |
| WO | 2019213592 A1 | 11/2019 | | |
| WO | 2019226650 A1 | 11/2019 | | |
| WO | 2019227080 A1 | 11/2019 | | |
| WO | 2021092210 A1 | 5/2021 | | |
| WO | 2021092249 A1 | 5/2021 | | |
| WO | 2021092254 A1 | 5/2021 | | |
| WO | 2021183680 A1 | 9/2021 | | |
| WO | 2021222257 A1 | 11/2021 | | |
| WO | 2021231705 A1 | 11/2021 | | |
| WO | WO-2022013318 A1 * | 1/2022 | | A61P 31/04 |
| WO | 2022055985 A1 | 3/2022 | | |
| WO | 2022098899 A1 | 5/2022 | | |
| WO | 2022/133532 A1 | 6/2022 | | |
| WO | 2022140630 A1 | 6/2022 | | |
| WO | 2022235799 A2 | 11/2022 | | |
| WO | 2022261498 A1 | 12/2022 | | |
| WO | 2023044068 A1 | 3/2023 | | |
| WO | 2023215798 A1 | 11/2023 | | |
| WO | 2024073588 A1 | 4/2024 | | |
| WO | 2024086532 A1 | 4/2024 | | |
| WO | 2024113057 A1 | 6/2024 | | |
| WO | 2023243835 A1 | 8/2024 | | |
| WO | 2024194876 A1 | 9/2024 | | |
| WO | 2024243637 A1 | 12/2024 | | |
| WO | 2024250022 A1 | 12/2024 | | |

OTHER PUBLICATIONS

J. Carbol et al., "Formulating Topical Products Containinig Live Microorangisms as the Active Ingredient", Pharmaceutical Technology, 42(3), pp. 32-36 (Mar. 1, 2018).
R.Y.K. Chang et al., "Hydrogel formulations containing non-ionic polymers for topical deliver of bacteriophages", International Journal of Pharmaceutics, vol. 605, pp. 1-7 (Jun. 30, 2021).
European Search Report issued Jan. 16, 2023 in European Patent Application No. 22183895.6.
Altamirano, Barr, "Phage Therapy in the Postantibiotic Era," Clin Microbiol Rev., 2019, vol. 32, No. 2, pp. e00066-18 (25 pages total).
Anurova et al., "Russian Journal of Biopharmaceuticals," Technological Processes for the Production of Ion-Exchange Resins, 2019, vol. 11, No. 2, pp. 30-33.
Baddour et al. "Infective Endocarditis in Adults: Diagnosis, Antimicrobial Therapy, and Management of Complications: A Scientific Statement for Healthcare Professionals From the American Heart Association," Circulation, 2015, vol. 132, pp. 1435-1486.
Carbol et al., "Formulating Topical Products Containing Live Microorganisms as the Active Ingredient," Pharmaceutical Technology Europe, 2018, vol. 30, No. 3, pp. 24-27.
Morello et al., "Pulmonary Bacteriophage Therapy on Pseudomonas aeruginosa Cystic Fibrosis Strains: First Steps Towards Treatment and Prevention," PLOS One, 2011, vol. 6, No. 2, pp. 1-9.
Hussain et al., "In vitro and in vivo study for antibacterial activity of endolysin-HEC gel and mixture gel on acne vulgaris caused by multidrug-resistant Staphylococcus aureus bacteria," Journal of Population Therapeutics and Clinical Pharmacology, 2023, pp. e242-e257.
Kasman et al., "Overcoming the Phage Replication Threshold: a Mathematical Model with Implications for Phage Therapy," Journal of Virology, 2002, vol. 76, No. 11, pp. 5557-5564.

(Continued)

*Primary Examiner* — Michelle F. Paguio Frising
(74) *Attorney, Agent, or Firm* — Greenberg Traurig, LLP; Melissa Hunter-Ensor; Nicholas R. Ballor

(57) ABSTRACT

The present invention provides a hydrogel comprising hydroxyethyl cellulose (HEC) and bacteriophages.

20 Claims, 34 Drawing Sheets

(56) References Cited

OTHER PUBLICATIONS

Figure 1:
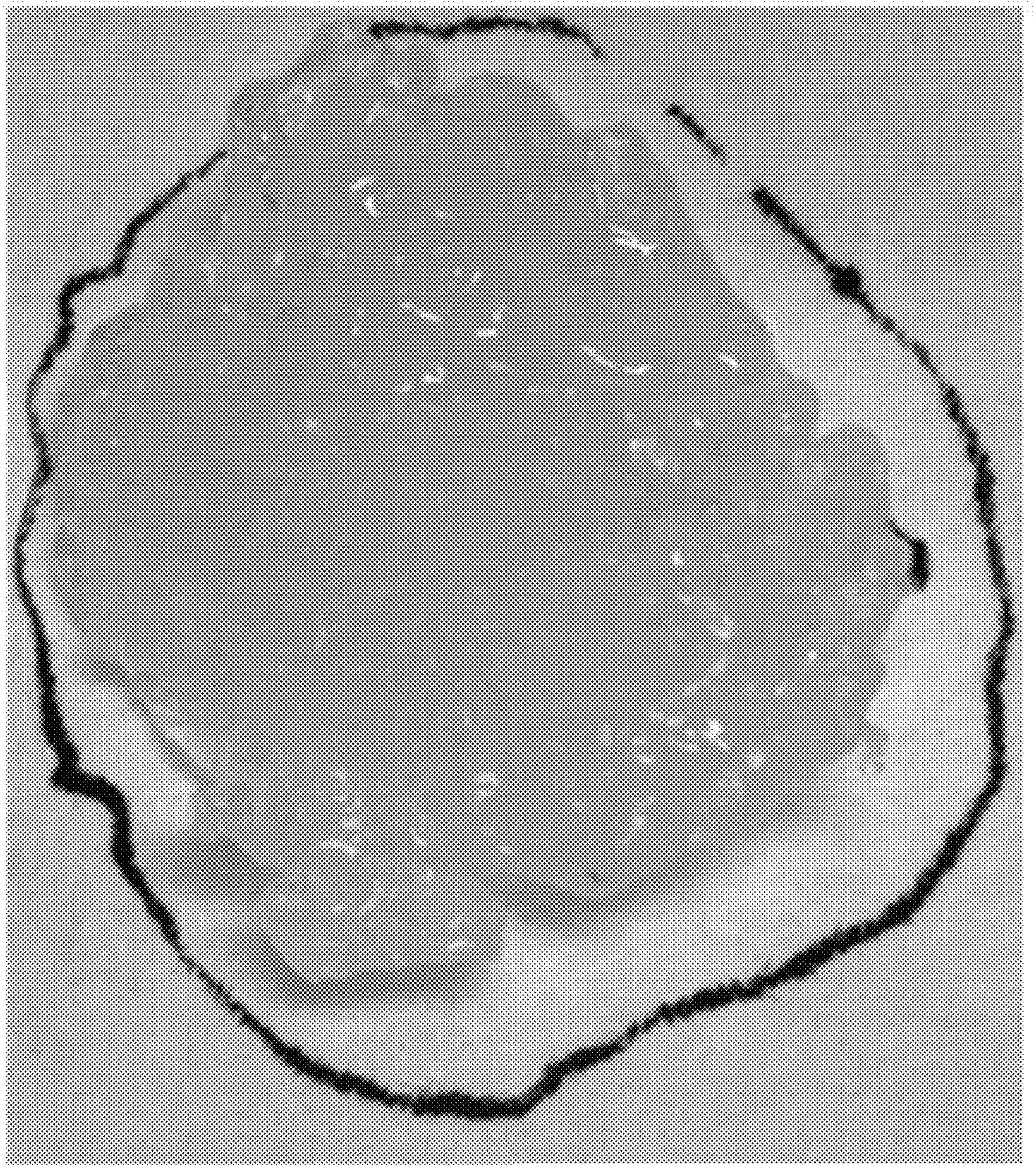

Kim et al., "FDG PET/CT for Early Detection and Localization of Left Ventricular Assist Device Infection: Impact on Patient Management and Outcome," JACC Cardiovasc Imaging, 2019, vol. 12, No. 4, pp. 722-729.
Kim et al., "Bacteriophage-Delivering Hydrogels: Current Progress in Combating Antibiotic Resistant Bacterial Infection," Antibiotics, 2021, p. Vol. 10, pp. 1-17.
Kirklin et al., "Eighth annual INTERMACS report: Special focus on framing the impact of adverse events," The Journal of Heart and Lung Transplantation, 2017, vol. 36, pp. 1080-1086.
Lam et al., "Therapeutic Effect of a Newly Isolated Lytic Bacteriophage against Multi-Drug-Resistant Cutibacterium acnes Infection in Mice," International Journal of Molecular Sciences, 2021, vol. 22, No. 13, pp. 1-14.
Narasimhaiah et al., "Therapeutic Potential of Staphylococcal Bacteriophages for Nasal Decolonization of Staphylococcus aureus in Mice," Advances in Microbiology, 2013, vol. 3 No. 1, pp. 52-60.
Malik et al., "Formulation, stabilisation and encapsulation of bacteriophage for phage therapy," Adv Colloid Interface Sci., 2017, vol. 249, pp. 100-133.
Rhoads et al., "Bacteriophage therapy of venous leg ulcers in humans: results of a phase I safety trial," Journal of wound care, 2013, vol. 18, No. 6, pp. 237-243.
Silva et al., "Newly isolated lytic bacteriophages for Staphylococcus intermedius, structurally and functionally stabilized in a hydroxyethylcellulose gel containing choline geranate: Potential for transdermal permeation in veterinary phage therapy," Research in veterinary science, 2021, vol. 135, pp. 42-58.
Szilagyi et al., "Infection in arterial reconstruction with synthetic grafts," Ann Surg., 1972, vol. 176, pp. 321-333.
Zühlke et al., "Postoperative Infektionen in der Gefäßchirurgie," In: Septische Gefäßchirurgie Blackwell Wiss Verlag, 1994, pp. 9-23.

* cited by examiner

Figure 23
CT: Body-ldCT 700mm
PT: [WB_CTAC] Body 676 mm
CT: 5/19/2021
PT: 5/19/2021
CT: Series: 2 / Slice: 129
PT: Series: 200190 / Slice: 129
Width:350 Level:35

HYDROXYETHYCELLULOSE GEL COMPOSITION COMPRISING BACTERIOPHAGES

This Application claims priority from Application EP 22183895.6 filed on Jul. 8, 2022 in European Patent Office. The entire contents of the Application EP 22183895.6 is incorporated herein by reference in its entirety.

The present invention relates to hydrogels comprising hydroxyethyl cellulose (HEC) and bacteriophages as well as lyophilizates thereof and to uses of such hydrogel or lyophilizate, especially in the treatment and prevention of bacterial infections.

With increasing antibiotics resistance, bacterial infections generally became an arising issue over the past years. This usually affects all medical fields, especially when a larger surface of a subject's body gets in contact with materials foreign to it.

This basically applies for example in the context of larger wounds resulting from surgery, especially skin surgery, which are exposed to potentially contaminated air, suture material or dressings. For example, the surgical removal of damaged skin or tissue from patients suffering from acne inversa or decubitus/pressure ulcer very often leaves behind large wounds. These usually cure slowly and have a huge risk of repeated bacterial infection, which is even increased by the fact that they need to cure open after wound debridement. Moreover, post-surgery, also hematogenous infections, which originate from already existing peripheric wounds, such as diabetic chronic wounds, may lead to severe issues.

Bacterial infections of vascular grafts represent a major burden in cardiovascular medicine, which is related to an increase of morbidity and mortality. Different factors that are associated to this medical field like patient frailty, biofilm formation or immunosuppression negatively influence antibiotic treatment, and, thereby, inhibit therapeutic success. Thus, further treatment strategies are required. Bacteriophage antibacterial properties were discovered 100 years ago, but the focus on antibiotics in Western medicine since the mid-twentieth century slowed the further development of bacteriophage therapy. Therefore, the experience and knowledge gained until then in bacteriophage mechanisms of action, handling, clinical uses and limitations were largely lost. However, the parallel emergence of antimicrobial resistance and individualized medicine result in the need of further means for the treatment of bacterial infections.

This especially applies to the treatment of bacterial infections in the context of surgery. In particular, both open and endovascular surgical cardiovascular repair carry the risk of nosocomial infection and a prosthetic vascular graft infection is generally tedious, related to other complications, and often acutely life-threatening. The prevalence of nosocomial infections in surgical patients ranges from 4% to 15% in patients requiring intensive care treatment. The standard treatment of resection and autologous vascular reconstruction can be prohibitively high-risk in compromised patients and alternatives are urgently required. In addition, prosthetic vascular graft infection is one of the most feared complications in cardiovascular surgery and associated with significant morbidity, mortality as well as increased hospitalization costs. The most common pathogenic bacteria are *Staphylococcus aureus, Staphylococcus epidermidis*, other coagulase-negative staphylococci, Enterobacterales, *Escherichia coli, Pseudomonas*, and corynebacteria. Bacteria often increase their virulence by attaching themselves to prosthetic material, protecting themselves from the local immune response and from antibiotics with the help of biofilms that inhibit phagocytosis and the current standard therapy. Moreover systemic antibiotic therapy is often inadequate because effective saturation concentrations can rarely be achieved in inflammatory periprosthetic tissue.

Bacteriophages (or simply 'phages'; from the Greek: "bacteria eater") are viruses that selectively infect bacterial cells and were first described in 1917 by the Canadian Felix Hubert d'Hérelle. They are quite stable in the environment and contribute significantly to the regulation of global bacterial mass. In principle, a bacteriophage can be found wherever its corresponding bacterium is but can only multiply where the host is. Bacteriophages are specific and almost always only affect strains within one bacterial species, rarely crossing species boundaries. Lytic bacteriophages initiate the lytic cycle of viral reproduction; phages kill their corresponding bacteria through lysis: once infected, the bacterium host cell then starts the process of reproduction, the destruction of the bacterium, and the release of new phage particles; this process is controlled by enzymes and an interaction of bacterial and phage genes. On the other hand, lysogenic phages initiate the lysogenic cycle: the bacteriophage nucleic acid is integrated into the host bacterium's genome or forms a circular replicon in the bacterial Clean Version of the Substitute Specification cytoplasm. Here the lytic circle is started by extern triggers, for example by UV-Light or warmth.

Bacteriophages are dynamic biological agents that multiply in the host bacteria and place different demands on clinical studies and complicate regulatory approval processes more suited to passive, chemical defined drugs like antibiotics. Although the therapeutically use of bacteriophages is common in the countries of the former Soviet bloc, there is a lack of randomized, placebo-controlled and double-blind studies that would provide scientifically usable data to allow regulatory approval in the Western hemisphere. An increasing number of case reports describe successful phage therapy to treat life-threatening infections. However, although some clinical studies have been undertaken, most failed to provide clear evidence of the effectiveness of phage therapy: one study assessing a phage cocktail against *E. coli* and *P. aeruginosa* infections in burn wounds was terminated early due to insufficient effectiveness.

Only bacteriophage solutions are currently available so topical application is difficult due to the adhesive and flow dynamics. Even if bacteriophages are successfully delivered to the site of infection, they can run into and onto the surrounding tissue, particularly in the case of circular application, such as infected anastomoses. Although this does not normally present a risk of local or systemic adverse reactions, it will compromise efficacy. Preservation of bacteriophages on prosthetic surfaces, for instance, is not known. It is essential that the bacteriophages remain in/at the place of application for sufficient time to ensure bacteriophage and bacterium interaction; semi-solid and solid formulations are needed.

In view of the above, it remains an object in the art to provide antibacterial compositions, which can for example be applied during surgery.

This object was solved by the present invention, which in a first aspect provides a hydrogel comprising hydroxyethyl cellulose (HEC) and bacteriophages.

The inventors have surprisingly found that a hydrogel comprising hydroxyethyl cellulose (HEC) and bacteriophages in medical applications shows superior properties in comparison to other hydrogels. In detail, it was unexpectedly found that among the most suitable gel forms tested, hydroxy-ethyl-cellulose (HEC) is the best gel former. In contrast to previous studies, it was found that a hydrogel comprising hydroxyethyl cellulose (HEC) provides a solid gel, which simultaneously can easily and painlessly be applied and spread e.g., on a patient's skin. In contrast to other gels tested, it concomitantly showed a firmness that allowed application of individual layer thicknesses. Previous studies state that the mesh size in a hydrogel comprising HEC allegedly is too small and HEC-based gels are not suitable for phage release applications as they showed poor release of infective phages (see e.g., Chang et al. Int J Pharm. 2021 Aug. 10; 605:120850). In contrast thereto, the inventors of the present invention could surprisingly show in vitro as well as in expanded accesses that the hydrogel of the invention comprising HEC does not only show the ability to keep phages, but also is capable of continuously releasing them in a retarded manner. This was shown indirectly in expanded accesses and animal experiments and directly in lyophilizate experiments. Furthermore, while kept in a hydrogel comprising HEC according to the invention, the phages were found to keep their lytic activity.

The following medical applications concerned the successful treatment of patients that were not suitable for extensive surgical approaches, patients that did not respond to common guideline treatment (such as the administration of conventional antibiotics due to antibiotic resistance) or patients that had bacterial infections at positions difficult to access (such as intra-aortic stent, TEVAR, or within a biofilm).

In view of the haptic, the good, uniform, even protective feel on the skin, as well as the properties of easy application, also in terms of a desired layer thickness, the following medical applications were focused on the superior hydrogel comprising HEC. Especially, the hydrogel of the invention comprising HEC showed convincing results in view of phage release for prevention of bacterial infections.

Successful treatments concerned bacterial infections in the field of cardiovascular medicine. First, a patient, who had a TEVAR, was successfully treated with extra- and endovascular bacteriophage application (Example 2).

Second, a patient with a chronically infected and occluded aorto-bifemoral Dacron® Bypass was also successfully treated with bacteriophages (Example 3). In this example, the infected implants were obviously clinically covered by a bacterial biofilm, which could not be completely removed mechanically (manually). This shows a significant advantage of the treatment of bacterial infections using a hydrogel according to the first aspect of the invention, which due to its abilities to localize at the biofilm in combination with retarded bacteriophage release allowed the effective and successive long-term treatment of the biofilm as well as the infection associated therewith. This also further corroborates the options of antibiotic systemic co-treatment by the hydrogel of the invention.

In a next step, the hydrogel comprising HEC and bacteriophages was tested in the context of skin surgery. A patient suffering from acne inversa after surgery showed improved wound healing when treated with a hydrogel comprising HEC and bacteriophages in comparison to hitherto common wound treatments (Example 6). A bacterial infection mouse model confirmed above-mentioned superior results of a hydrogel comprising HEC and bacteriophages in wound healing (Example 7). Finally, it could further be shown that also a lyophilizate of a hydrogel comprising HEC and bacteriophages shows the desired bacteriophage release and activity (Example 4 and 5).

To sum up, the inventors disproved prior art and could show that hydrogels comprising HEC are an excellent tool being able to keep phages, maintain their lytic activity and retardedly release them.

The inventors could further disprove the common guidelines for implant removal and reimplantation. In contrast thereto, the new developed approach using a hydrogel or a lyophilizate according to the invention allows minimally invasive surgery, keeping infected implants in situ and increasing antibiotic sensitivity.

Also in the field of biofilms, the hydrogel or the lyophilizate according to the invention is advantageous in comparison to previously applied methods. The hydrogel or the lyophilizate according to the invention allow destruction of the biofilm by closely adhering to its surface and retarded release of phages.

In comparison to so far applied treatment methods using aqueous and individual phage solutions, the hydrogel or the lyophilizate according to the invention showed strongly improved wound healing by the factor of 2.5. in mouse experiments. The successful treatment was conducted intracorporal as well as cutaneously.

Moreover, instead of an individual therapy, the hydrogel or the lyophilizate of the present invention provide a standard therapy with a standard phage cocktail for treating and/or preventing bacterial infections.

Finally, while the hydrogel or the lyophilizate of the present invention show all these advantages, they did not show any unwanted side effects, also not when applied intravascular.

In a first aspect, the present invention provides a hydrogel comprising hydroxyethyl cellulose (HEC) and bacteriophages.

In the context of the present invention (see Example 1), the inventor has found that HEC is' a gel forming agent which is especially suitable for preparing gels with the desired haptic and other properties. Especially, the hydrogel of the present invention can be steam sterilized, which is an important property for the envisaged use in the treatment of bacterial infections, especially during surgery.

In addition, as shown in Example 2, it could be shown that the claimed composition is particularly effective in treating bacterial infections when applied during surgery.

In the context of the present invention, the terms "phage (s)" and "bacteriophage(s)" are used interchangeably.

In the context of the present invention, the following abbreviations are used:

AMR; Antimicrobial resistance
CT Computed tomography
EVAR Endovascular aortic repair
MRSA Methicillin-resistant *Staphylococcus aureus*
PET Positron emission tomography
SAVR Surgical aortic valve replacement
TAVR Transcatheter aortic valve replacement
TEVAR Thoracic endovascular aortic repair As discussed above, bacteriophages are well-known antibacterial agents. In the context of the present invention, any type of bacteriophages can be used. It is also possible to prepare customized gel preparations where the type of bacteria to be treated is determined and then the corresponding bacteriophages are selected.

In another embodiment of the present invention, a standardized bacteriophage composition is used which are active against preselected types of bacteria. For example, the bacteriophages contained in the hydrogel of the present invention may be active against *Staphylococcus aureus*, *Staphylococcus epidermidis*, other coagulase-negative staphylococci, Enterobacterales, *Escherichia coli, Pseudomonas*, and corynebacteria. Such bacteriophages are known in the art, as discussed above.

In the context of the present invention, it is preferred to use lytic bacteriophages. This has the advantage that that the antibacterial effect of the bacteriophages starts immediately when encountering a corresponding bacterium. The bacteriophages contained in the hydrogel according to the first aspect, may be thermostable and/or cryostable. When the bacteriophages contained in the hydrogel according to the first aspect are cryostable, they preferably are stable even at low temperatures, such as from about minus 90° C. to minus 20° C. In another preferred embodiment, the bacteriophages in the hydrogel of the present invention are thermostable. In another preferred embodiment, the bacteriophages are cryostable.

The concentration of the phages in the hydrogel can be any concentration, which is effective for the treatment of the bacterial infection and may vary depending on the bacteriophages used and on the expected bacterial concentration.

As a minimum, a phage concentration of $10^2$ pfu/ml may for example be used.

In one embodiment, the concentration of the bacteriophages is between $10^2$ pfu/ml and $10^8$ pfu/ml, preferably between $10^4$ pfu/ml to $10^8$ pfu/ml or $10^5$ pfu/ml to $10^7$ pfu/ml.

In an also preferred embodiment, the concentration of the bacteriophages in the hydrogel is from $10^2$ pfu/ml to $10^8$ pfu/ml, preferably from $10^2$ pfu/ml to $10^7$ pfu/ml, more preferably from $10^2$ pfu/ml to $10^6$ pfu/ml, most preferably from $10^2$ pfu/ml to $10^{5,5}$ pfu/ml.

Before adding the phages to the composition of the invention, the bacteriophages preferably are sterilized, more preferably steam sterilized. The initial phage concentration is may reduced accordingly during the sterilization process. This reduction of the phage quantity is calculated beforehand, so that the final product may have a phage concentration of at least $10^2$ pfu/ml.

In another preferred embodiment, the bacteriophages are sterilized via sterile filtration.

The bacteriophages may be added in a solution to the hydrogel of the present invention. For example, when preparing the hydrogel of the present invention, the bacteriophage solution may be 50%, and the HEC gel stock solution (optionally with other ingredients, see below) may also be 50%.

The bacteriophage preparation may be produced according to the applicable GMP guidelines.

The hydrogel of the present invention is a hydoxy-ethyl-cellulose (HEC) containing hydrogel.

Hydroxy-ethyl-cellulose (=HEC) has the following chemical formula

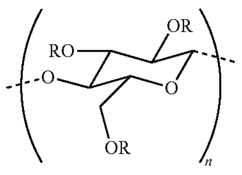

R═H or $CH_2CH_2OH$ (source: apothekenwiki.com/wp-content/uploads/2017/12/Hydroxyethylcellulose-Strukturformel.png)

HEC is known in the art. In the context of the present invention, HEC of any suitable length can be used. Especially, n can be varied between 300 and 15.000, more preferable between 500 and 10.000 most preferred between 2.000 and 8.000.

In the context of the present invention, HEC is used as a gel former because it could be shown in the context of the present invention that HEC leads to a stable gel scaffold on an aqueous basis. The gel matrix formed by the HEC offers sufficient space to retain the defined concentration of phage in a distribution that is conducive to release. In addition, the viscosity of the end product is easily adjustable via the concentration of the gel former, so that the change in the HEC percentage offers further product possibilities with the same material composition. Furthermore, HEC is well known for its pharmaceutical use and has a low allergenic potential.

Of the other gel formers often used in the pharmaceutical industry, HEC is the only one that can be steam sterilized, as shown in the attached example. This sterilization process increases the viscosity of the gel, so that this "viscosity gain" may be considered when preparing the composition of the present invention. Through the water reabsorption of the product from interstitial body water under additional influence of body/skin temperature, the product can float up at the application site. Through this process of passing through various viscosity levels to aqueous, the phages are released and, as they continue to spread at the site of application and in ever smaller doses, act beyond:

Another reason for the use of hydroxyethyl cellulose is the low sensitivity of the gel former and consequently of the finished product to changes in pH and to electrolytes. HEC gel production and equally phage HEC gel production are easy, cheap and fast to realize both in manual manufacture and industrial scale handling. No special equipment or surfaces are required.

The hydrogel of the present invention preferably comprises 3 to 10% HEC, more preferably 5 to 8% HEC or 6 to 7% HEC, most preferably 6.5% HEC.

In a preferred embodiment, the hydrogel of the first aspect comprises 3% to 10% HEC, preferably 5 to 9% HEC, more preferably 6 to 9% HEC, especially preferred 6% to 7% HEC and most preferably 6.5% HEC.

The hydrogel of the present invention may be prepared by mixing the individual components and adding water to obtain the final concentration. In principle, the preparation of HEC hydrogels is known in the art.

Gel manufacturing is performed manually or in technical processes and is known in the art. For example, the dissolving ingredients may be dissolved in a first part of water. Successively HEC may be incorporated in the water under moderate stirring. At least the rest of needed water may be given into the gel mass under further moderate stirring. After preparing the hydrogel, the hydrogel may be sterilized, preferably steam sterilized.

The bacteriophages may be given into the gel for example in form of a bacteriophage solution. Mechanical forces may be needed to dissolve the phages into the gel matrix. That may be done by stirring the composition while adding the bacteriophage solution or by a two-syringe-technique: Therefore one syringe may contain the bacteriophage solution, a second may provide the gel. Through a connector the gel and bacteriophage solution may be brought together, by first pressing the phages solution into the gel. The process may be replied multiple times vice versa.

In a preferred embodiment, the hydrogel further comprises $CaCl_2$ and glycerol.

Calcium may serve to stabilize and thus maintain the activity of the bacteriophages. Calcium may be added to the composition in the form of readily soluble calcium chloride but other Calcium salts may also be used. By dissolving the $CaCl_2$ in the composition, especially in the contained water, the calcium is made available to the phages as calcium ions ($Ca^{2+}$). Calcium chloride has only low chemical reactivity on its own, does not affect the adjusted product pH and, in the quantities described below (for example in a concentration between 10% and 33%), has no relevant influence with regard to osmotic processes.

The hydrogel of the present invention may comprise 10 to 33% $CaCl_2$, preferably 15 to 25% or 17 to 23%, and more preferably 20 to 22%, most preferably 21.5%.

Glycerol may be used to increase the adhesive properties and to retard product liquefaction under the influence of body temperature and fluid, since it may serves as a lubricant, spreading agent and adhesion promoter. Glycerol is also hygroscopic and thus not only supports systematic degradation and phage release over the surface of the applied PhaTEC-drug, but it also contributes to residue-free degradation of the product. As in the case of surgical sutures, the inclusion of glycerol makes it a self-absorbable product.

The hydrogel of the present invention may comprise 6 to 22% glycerol, preferably 8 to 18%, more preferably 10 to 16% or 12 to 15%, most preferably 13.5% glycerol.

Glycerol may be added to the composition in the form of glycerol 85%.

In a preferred embodiment, if the hydrogel of the first aspect comprises $CaCl_2$ and glycerol, the hydrogel may comprise 10% to 33% $CaCl_2$, preferably 15% to 25% or 17% to 23%, and more preferably 20% to 22%, most preferably 21.5%.

In a further preferred embodiment, if the hydrogel of the first aspect comprises $CaCl_2$ and glycerol, the hydrogel may comprise 6% to 22% glycerol, preferably 8% to 18%, more preferably 10% to 16% or 12% to 15%, most preferably 13.5% glycerol.

In an also preferred embodiment, if the hydrogel of the first aspect comprises $CaCl_2$ and glycerol, the hydrogel may comprise a) 10% to 33% $CaCl_2$, preferably 15% to 25% $CaCl_2$ or 17% to 23% $CaCl_2$, more preferably 20% to 22% $CaCl_2$, and most preferably 21.5% $CaCl_2$; and additionally b) 6% to 22% glycerol, preferably 8% to 18% glycerol, more preferably 10% to 16% glycerol or 12% to 15% glycerol, most preferably 13.5% glycerol.

In a further preferred embodiment, the hydrogel of the present invention further contains a buffer. Buffers suitable in the context of the present invention include Tris-HCl (pH=7.4), sodium chloride and magnesium chloride.

The hydrogel of the present invention may further comprise other salts like sodium chloride; magnesium chloride, calcium chloride and potassium chloride.

The hydrogel of the present invention may preferably have a physiological pH, for example a pH of 7, 7.2, 7.4, 7.6 or 7.8. Using a buffer to ensure a physiological pH may also be helpful to attenuate the pH differences in infected, inflammatory tissues.

In an especially preferred embodiment, the hydrogel of the present invention comprises a buffer comprising sodium chloride, magnesium chloride (x7H2O) and Tris-HCl, pH=7.4.

In another preferred embodiment, the hydrogel according to the first aspect of the invention has a pH of 7.0 to 7.8, preferably of 7.1 to 7.6, more preferably of 7.2 to 7.5, most preferably a pH of 7.4.

The HEC stock solution for preparing the HEC hydrogel of the present invention may comprise as an example (based on 100 g):

HEC (Hydroxy-ethyl-cellulose): 13 g=13%
$CaCl_2$-Solution*: 43 g=43%
Glycerol 85%: 27 g=27%
Water: 17 g=17%

In a Preferred Embodiment, the Hydrogel of the Present Invention Comprises $10^2$ pfu/ml to $10^8$ pfu/ml bacteriophages,
3 to 10% HEC,
10 to 33% $CaCl_2$, and
6 to 22% glycerol.

In a further preferred embodiment, the hydrogel of the present invention comprises $10^2$ pfu/ml to $10^8$ pfu/ml bacteriophages,
5 to 8% HEC,
10 to 33% $CaCl_2$, and
6 to 22% glycerol.

In a preferred embodiment of the present invention, the hydrogel of the present invention comprises $10^4$ pfu/ml to $10^8$ pfu/ml bacteriophages,
3 to 10% HEC,
15 to 25% $CaCl_2$, and
8 to 18% glycerol.

In a more preferred embodiment of the present invention, the hydrogel of the present invention comprises $10^5$ pfu/ml to $10^7$ pfu/ml bacteriophages,
6.5% HEC,
21.5% $CaCl_2$, and
13.5% glycerol.

In another preferred embodiment, the hydrogel according to the first aspect of the invention comprises $10^2$ pfu/ml to $10^8$ pfu/ml bacteriophages,
3 to 10% HEC,
10 to 33% $CaCl_2$, and
6 to 22% glycerol;
preferably
$10^2$ pfu/ml to $10^7$ pfu/ml bacteriophages,
5 to 8% HEC,
10 to 33% $CaCl_2$, and
6 to 22% glycerol;
more preferably
$10^2$ pfu/ml to $10^6$ pfu/ml bacteriophages,
3 to 10% HEC,
15 to 25% $CaCl_2$, and
8 to 18% glycerol;
or
$10^2$ pfu/ml to $10^{5,5}$ pfu/ml bacteriophages,
3 to 10% HEC,
15 to 25% $CaCl_2$, and
8 to 18% glycerol;
and most preferably
$10^2$ pfu/ml to $10^{5,5}$ pfu/ml bacteriophages,
6.5% HEC,
21.5% $CaCl_2$, and
13.5% glycerol.

The water used in the composition of the invention may be Aqua ad injectabilia.

In an exemplary embodiment, the hydrogel of the present invention is prepared using the following ingredients.

| | defined ingredient used | percentage (by weight) [%] used |
|---|---|---|
| Bacteriophages | Bacteriophages solution containing a concentration of $10^7$ pfu/ml | 50 |
| Hydroxy-ethyl-cellulose (HEC) | Natrosol 250 HX | 6.5 |
| $CaCl_2$ | $CaCl_2$-Soltution containing a concentration of 73.5 g/L | 21.5 |
| Glycerol | Glycerol 85% | 13.5 |
| Water | Aqua ad injectabilia | 8.5 |

In a preferred embodiment, the hydrogel of the present invention has a viscosity of 1000 mPas up to 100.000 mPas; preferably 10.000 to 80.000 mPas, more preferably 40.000 to 80.000 mPas or 40.000 to 60.000 mPas or.

In a preferred embodiment of the present invention, the hydrogel of the invention is sterile. Preferably, the hydrogel has been steam-sterilized.

Sterility may be achieved by sterilizing the HEC hydrogel and the bacteriophage solution separately, or by sterilizing the hydrogel of the present invention, i.e., the hydrogel comprising hydroxyethyl cellulose (HEC) and bacteriophages.

In a second aspect, the present invention relates to a lyophilizate of the hydrogel according to the first aspect.

Thereby, the term "lyophilizate of the hydrogel" describes any product received by freeze-drying a hydrogel according to the first aspect of the invention. The term "freeze-drying" describes any low temperature dehydration process. Usually, the temperature is lowered at least until freezing of the water is achieved and pressure is lowered leading to sublimation of water. Methods for freeze-drying are well-known to the person skilled in the art.

Starting point may be the hydrogel according to the first aspect of the invention. Before the freeze-drying process is started, the gel usually is stored in a cool place, such as a fridge; e.g., by at most 8° C. until the freeze-drying process is started.

At the start of the freeze-drying process, the hydrogel of the first aspect of the invention may be filled into a (sterile) container that usually already has the desired product shape. These containers can be, among others, cups, which are made from a foil designed for this purpose, e.g., using a thermoforming technique. The thickness of the resulting product may also be predetermined in this process step and usually is a result of the filling height of the container.

The freezing and the duration of the applied vacuum, as well as its intensity, must generally be adapted to the product size, i.e. gel volume. The freeze-dryers (equipment) used may also have an influence on the process parameters to be applied, e.g. due to different capacities. Consequently, the following process data are to be regarded as examples.

For example, in a first step, the hydrogel may be frozen at a temperature of minus 20° C. for 2 hours. In a second step, the main drying may then be carried out at 2.5 mbar at minus 10° C. for approx. 40 h. A third step may comprise secondary drying at >1 mbar and 10° C. and may take place for approx. 20 h.

In general, it may be considered that the freezing process is crucial for the production of phage-containing freeze-dried products: it should be fast, and a highly amorphous product should be obtained. A fast freezing process also generally ensures that the lytic activity of the bacteriophages is maintained. Regardless of the volumes to be frozen, process times for freezing are usually freezing times <5 h, more preferably freezing times <2 h and more preferably freezing times <1.5 h.

Further drying times depend mainly on the performance of the equipment used and usually have only a minor influence on the properties of the resulting product.

Preferably, the method of preparing a lyophilizate of the hydrogel according to the first aspect of the invention comprises the steps of a) providing a hydrogel according to the first aspect of the invention;

b) freezing the hydrogel of step a) at a temperature of at most −10° C., preferably −20° C., more preferably −40° C. and most preferred −60° C.; for <5 h, preferably <2 h, more preferably <1.5 h and most preferred ≤1 h;

c) performing a main drying of the frozen hydrogel of step b) at ≤2.5 mbar at ≤10° C. for approx. 40 h, preferably at 1.5 mbar at −30° C. for approx. 40 h; d) performing a secondary drying at >1 mbar and 10° C. for approx. 20 h.

In order to maintain an elastic state, the resulting lyophilizate preferably has a remaining water content of >2%.

In general, the resulting lyophilizate may comprise
$10^2$ pfu/ml to $10^8$ pfu/ml bacteriophages,
5 to 25% HEC,
24 to 80% $CaCl_2$, and
13 to 50% glycerol;
preferably,
$10^2$ pfu/ml to $10^8$ pfu/ml bacteriophages,
10 to 20% HEC,
40 to 60% $CaCl_2$, and
20 to 40% glycerol;
more preferably,
$10^2$ pfu/ml to $10^8$ pfu/ml bacteriophages,
13 to 17% HEC,
45 to 55% $CaCl_2$, and
25 to 35% glycerol;
mostly preferred,
$10^2$ pfu/ml to $10^8$ pfu/ml bacteriophages,
14 to 16% HEC,
51 to 53% $CaCl_2$, and
30 to 33% glycerol.

Examples for the Composition of a Hydrogel and a Resulting Lyophilizate:

| Products | in: Gel upper & lower limit | in: Lyophilizate |
|---|---|---|
| Bacteriophages | $10^2$ to $10^8$ pfu/ml | $10^2$ to $10^8$ pfu/ml |
| HEC | 3 to 10% | ≈15% |
| $CaCl_2$ | 10 to 33% | ≈52% |
| Glycerol | 6 to 22% | ≈31% |

Preferably, the hydrogel according to the first aspect does not comprise any preservative system. More preferably, the hydrogel according to the first aspect does not comprise methylparaben, propylparaben, phenoxyethanol and/or potassium sorbate.

Sterilization of a Freeze-Dried Hydrogel:

In the context of medical applications, the objective generally is the provision of a sterile product, especially when the product is designed for implantation in the body, for example in the case of anastomoses and for the packing of wound cavities. However, the obligatory characteristic of sterility is generally determined by the intended use of the product, so that non-sterile products can also be reasonable.

Sterility of freeze-drying can be achieved by a sterile freeze-drying process using the previously sterilized bacteriophage-containing hydrogel. In addition, according to the laboratory results for the gel described, other types of sterilization, such as steam sterilization is also possible, especially, as the steam of steam sterilization does not enter into direct product contact and thus no water/water vapor is introduced into the product. Further aspects, such as the support pressure to be set in the steam sterilization process, usually must be taken into account.

Practically, when applied to a subject's body, a lyophilizate of a hydrogel according to the second aspect usually decomposes. First, the lyophilizate of a hydrogel swells back to gel (=semi-solid) state by body heat and water. In a second step, the gel of the first step, is generally further diluted by body water and turns into a liquid state. Finally, the diluted liquid hydrogel is physiologically degraded and excreted.

In comparison to a hydrogel comprising HEC and bacteriophages, a lyophilized product of the same hydrogel turned out to have many advantages. For example, a lyophilized product of the bacteriophage-containing hydrogel showed a (strongly) retarded release of bacteriophages, which is further determinable via gel composition and highly desired when e.g. treating infected wounds. Moreover, in comparison to a hydrogel comprising HEC and bacteriophages, a lyophilized product of the same hydrogel is much easier cuttable and stretchable as well as better modulatable and adaptable. It is further very elastic, so there is no compromising of physiologically dynamic structures.

Moreover, shape and thickness of the product, and thus the period of the phage, can be easily determined via the manufacturing process (e.g. also depending in the amount of hydrogel freeze-dried, etc.). Further, during application, coverages (if necessary with the aid of suture material) and surface restorations are possible, among other things. Further, due to the sterilization possibilities of the gel, the lyophilizate (=freeze-drying) is also sterile from a sterile production.

In a third aspect of the present invention, the invention relates to the hydrogel according to the first aspect of the invention or the lyophilizate according to the second aspect of the invention for use in a method of treating and/or preventing a bacterial infection.

Typical clinical fields, where infections often occur, which may be treated using a hydrogel according to the first aspect or a lyophilizate according to the second aspect, are e.g., cardiac surgery (such as artificial heart, driveline, artificial heart valves), vascular surgery (such as vascular implant, dialysis shunt), orthopedics (especially accident orthopedics) (such as the complete field of endoprosthetics e.g., knee and hip total endoprosthesis (TEP)), dermatology (such as akne inversa) and emergency medical services (such as wound dressing)

Likewise, the present invention relates to a method for treating and/or preventing a bacterial infection in a subject, wherein the hydrogel according to the first aspect of the present invention or the lyophilizate according to the second aspect of the invention is applied to the subject.

In a preferred embodiment of the third aspect, the hydrogel of the first aspect or the lyophilizate of the hydrogel of the second aspect is applied during surgery.

The subject may be any animal, but preferably, the subject is a mammal, more preferably a human.

The hydrogel according to the first aspect of the present invention or the lyophilizate according to the second aspect of the invention can be used to treat and prevent a bacterial infection. According to the invention, the term "treatment" means that bacteria, which are already present, are counteracted by the bacteriophages contained in the hydrogel, while the term "prevention" means that the bacteria are not yet present when the hydrogel or the lyophilizate is applied.

The hydrogel or the lyophilizate may be applied to any accessible surface of the subject. This includes but not limited to the skin or any accessible mucosa of the subject. The hydrogel or the lyophilizate of the present invention is especially suitable for treating a bacterial infection in a wound.

In a preferred embodiment, the hydrogel or the lyophilizate of the hydrogel for use according to the third aspect is applied to a surgical site, an implant, an anastomosis, a wound; an abrasion, a cut, a stab, a non-intact skin tissue and/or mucosal tissue, an entrance point of a catheter, a covering of sterile material, a wound and/or implant coverage, and/or suture material.

The hydrogel may be applied by any possible means. These include, but are not limited to manual application, application through a syringe, through a needle, through a catheter. Similarly, also the lyophilizate may be applied by any possible means. These include, but are not limited to manual application or application through a tool, such as forceps. Distribution of the hydrogel or the lyophilizate is mainly done by hand or any helping device to cover the sites/areas to be covered by the product.

In addition, the hydrogel or the lyophilizate may be applied to any implant which is to be attached or inserted into the body of the subject or which has already been inserted into the subject.

In a preferred embodiment, the hydrogel or the lyophilizate of the hydrogel for use according to the third aspect is used to treat and/or prevent a bacterial infection of an implant.

In detail, therapy using a hydrogel according to the first aspect or a lyophilizate according to the second aspect, turned out to be especially useful and promising in the field of infections of implants. According to the prescribed guidelines of treatment, each material infected must be removed and replaced by autologous material, which is not always possible. Especially, when the reoperation is in the cardiovascular field, it is very often unlikely that the subject will survive such surgeries. As the hydrogel according to the first aspect or the lyophilizate according to the second aspect can be applied minimally invasive, their use significantly increases the odds of a subject's survival. Very often, implants are also not autologously replaceable (such as artificial hearts, pacemaker, etc.). In such cases, it is highly advantageous that the implants when treated with the hydrogel or the lyophilizate according to the invention, can be left in situ and allow treatment of the infection of the infection in situ as well.

Thereby, in a further preferred embodiment of the present invention, the hydrogel or the lyophilizate of the hydrogel for use according to the third aspect may be directly applied to a surface of the implant, either outside of a subject's body or in a subject's body.

According to the invention, the implant may be a joint prosthesis, vascular prosthesis, heart valve, catheter, an artificial heart, a dental implant, and a minimally invasive heart valve TAVI.

In preferred embodiment of the third aspect, the implant is an endoprosthetic (preferably a joint prosthesis, more preferably a knee or hip total endoprosthesis), a vascular prosthesis, a heart valve, a catheter, an artificial heart, a driveline, a dialysis shunt, a dental implant, and/or a minimally invasive heart valve transcatheter aortic valve implantation (TAVI).

In a further preferred embodiment, the hydrogel or the lyophilizate of the hydrogel for use according to the third aspect is used to treat and/or prevent prosthetic vascular graft infection.

The medical areas where the hydrogel or the lyophilizate of the present invention may be applied include, but are not limited to surgery, orthopedics, radiology, nephrology, diabetics for example the superinfected diabetic foot syndrome, dermatology, cardiology, wound care, nursing facilities/services, and ambulance service.

Possible indications for the hydrogel or the lyophilizate of the invention are for example surgical sites, implants, anastomosis, wounds, for example deep wounds or wound holes, abrasions, cuts, stabs, non-intact skin tissue and mucosal tissue, decubitus/pressure ulcer, entrance points of catheters, e.g. ureter-/IV-catheter, covering of sterile material, wound and implant coverage, and suture material. Thereby, the term "decubitus/pressure ulcer" may describe any type of bedsore.

In a preferred embodiment of the invention, the hydrogel or the lyophilizate of the present invention is applied during surgery.

It has been shown in the present invention (see Examples 2 and 3) that the hydrogel is of the invention is especially useful for treating and preventing a bacterial infection when applied during surgery.

During surgery, the hydrogel or the lyophilizate of the invention can be applied by all possible means. For example, the bacteriophage gel can be applied manually and distributed in the same way, mainly by the surgeon while surgery or by any other person, especially when applied outside of the body, e.g. to wounds or skin.

Moreover application and distribution at/on the desired site/area can be done by all helping devices, mostly syringes, needles and catheters. So it is possible to apply the bacteriophages gel at minimal invasive interventions or in body/wound holes.

Because of the viscosity and the possibilities: to adapt the viscosity to the circumstances found e. g. while surgery, especially when the two-syringe technique in case of a hydrogel is used, and to the robustness of the product, which is provided by the duo of galenic and bacteriophages, all possibilities of application can be used.

In a preferred embodiment, the hydrogel or the lyophilizate of the hydrogel for use according to the third aspect is applied to a surface of a subject's body or to a surface of an implant manually and/or using one or more helping devices, preferably one lor more syringes, needles and/or catheters.

In an especially preferred embodiment of the present invention, as already mentioned above, the hydrogel or the lyophilizate of the present invention is used to treat and/or prevent a bacterial infection of an implant. In this embodiment of the invention, the hydrogel or the lyophilizate of the invention can be directly applied to the implant, either outside the body or in the body, e.g. during surgery.

In an also preferred embodiment, the hydrogel or the lyophilizate of the hydrogel for use according to the third aspect is used to treat and/or prevent a bacterial infection resulting from skin surgery, preferably resulting from skin surgery related to acne inversa treatment or decubitus/pressure ulcer.

In general, the hydrogel or the lyophilizate of the hydrogel for use according to the third aspect may be used to treat and/or prevent a bacterial infection resulting from any kind of skin surgery. This means that whenever during any kind of skin surgery, a wound is formed, which especially due to its size or location may be challenging to be cured without any issues of bacterial infection, a hydrogel according to the first aspect or a lyophilizate according to the second aspect may be applied to treat and/or prevent a bacterial infection to support wound healing.

Examples for such wounds are well known to the person skilled in the art, such as wounds resulting from skin biopsy, electrosurgery, cautery, skin flaps, skin grafting, Mohs microscopically controlled excision, cryotherapy (e.g. with liquid nitrogen), excision of skin lesions, liposuction, vitiligo surgery, acne inversa treatment or decubitus/pressure ulcer.

In a fourth aspect, the invention relates to a method of preparing a hydrogel comprising hydroxyethyl cellulose (HEC) and bacteriophages comprising the steps of a) providing HEC in a solid state of matter, b) dissolving solid HEC of step a) in a liquid component comprising water and bacteriophages, and c) optionally adding water until the desired viscosity is reached.

All aspects related to the first, second and third aspect of the invention, especially when they are related to features of the hydrogel, hydrogel preparation and bacteriophages, also apply to this fourth aspect of the invention.

Finally, the present invention also relates to a method of treating and/or preventing a bacterial infection comprising the use of the hydrogel according to the first aspect or the lyophilizate according to the second aspect.

Preferably, in the method of treating and/or preventing a bacterial infection, the hydrogel or the lyophilizate of the hydrogel is applied during surgery.

Also preferably, in the method of treating and/or preventing a bacterial infection, the hydrogel or the lyophilizate of the hydrogel is applied to a surgical site, an implant, an anastomosis, a wound, an abrasion, a cut, a stab, a non-intact skin tissue and/or mucosal tissue, e.g. an entrance point of a catheter, a covering of sterile material, a wound and/or implant coverage, and/or suture material.

More preferably, in the method of treating and/or preventing a bacterial infection, the hydrogel or the lyophilizate of the hydrogel is used to treat and/or prevent a bacterial infection of an implant.

Most preferred, in the method of treating and/or preventing a bacterial infection, wherein the hydrogel or the lyophilizate of the hydrogel is used to treat and/or prevent a bacterial infection of an implant, the hydrogel or the lyophilizate of the hydrogel is directly applied to a surface of the implant, either outside of a subject's body or in a subject's body.

In particular, in the method of treating and/or preventing a bacterial infection, the implant may be a joint prosthesis, vascular prosthesis, heart valve, catheter, an artificial heart, a dental implant, and/or a minimally invasive heart valve transcatheter aortic valve implantation (TAVI).

Especially, when the present invention relates to a method of treating and/or preventing a bacterial infection, the hydrogel or the lyophilizate of the hydrogel is used to treat and/or prevent prosthetic vascular graft infection.

Preferably, when the present invention relates to a method of treating and/or preventing a bacterial infection, the hydrogel or the lyophilizate of the hydrogel is used to treat and/or prevent a bacterial infection resulting from skin surgery, preferably resulting from skin surgery related to akne inversa treatment or decubitus/pressure ulcer.

Also preferably, when the present invention relates to a method of treating and/or preventing a bacterial infection, the hydrogel or the lyophilizate of the hydrogel is applied to a surface of a subject's body or to a surface of an implant manually and/or using one or more helping devices, preferably one lor more syringes, needles and/or catheters.

The invention is further illustrated by the attached examples and figures, which are intended to explain, but not to limit the present invention.

FIGURE LEGENDS

FIG. 1: Na-Hyaluronat gel on filter before stored for 24 h at 37° C. The gel is much too firm to be spread well on the filter paper and shows an agglomerate as a result of the stiffness of the gel.

Figure 2:
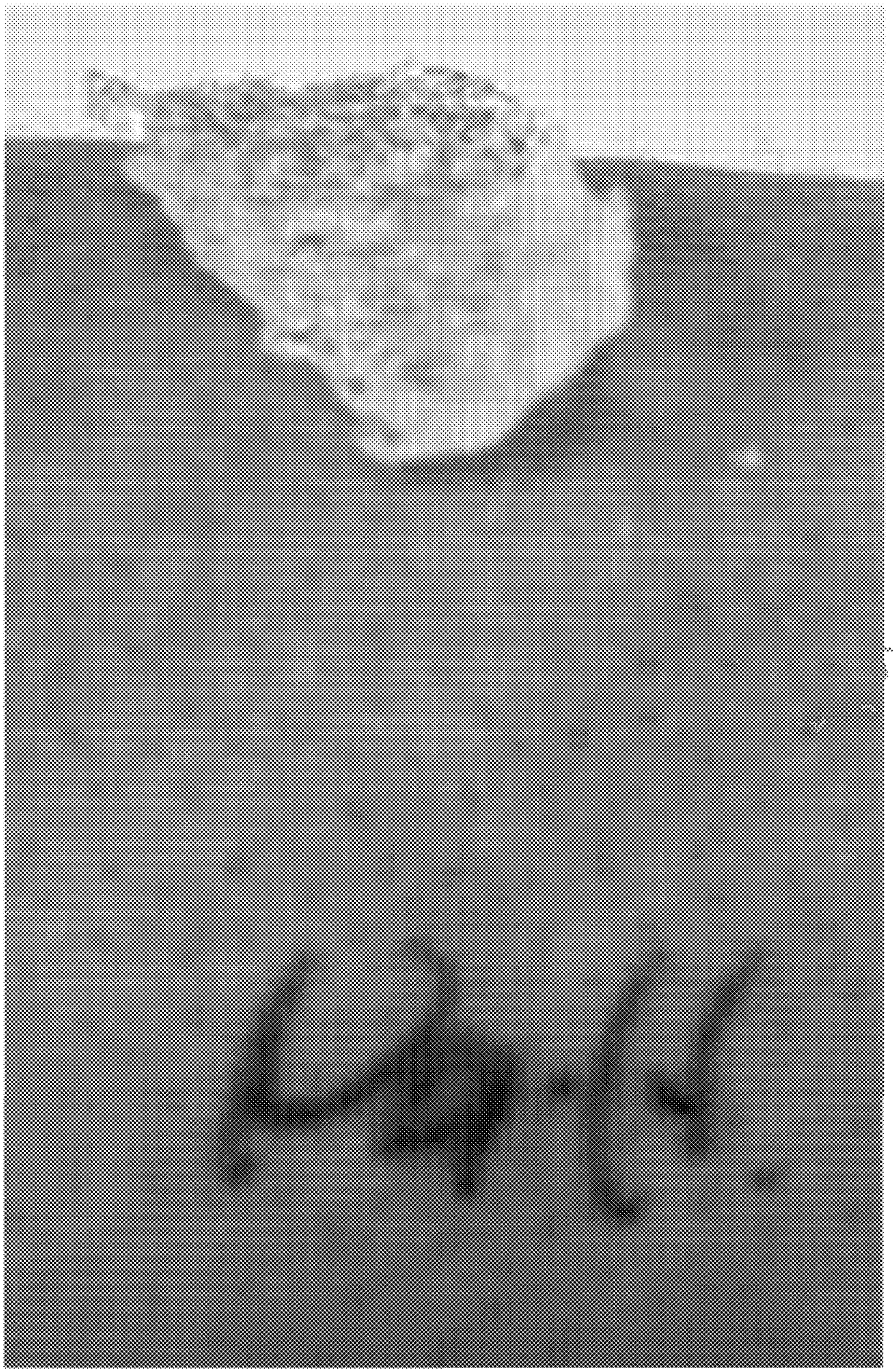

FIG. 2: Na-Hyaluronat gel on skin: the gel shows stiffness even on the skin. Tries of application and spreading on the shown arm were painful, due to the firm condition of the gel.

Figure 3:

FIG. 3: Carbomer gel on skin: the gel shows a highly adhesive character. Spreading on the skin difficult. Moreover, application and spreading was painful, due to the stickiness. A wanted layer of gel has not been applicable.

Figure 4:
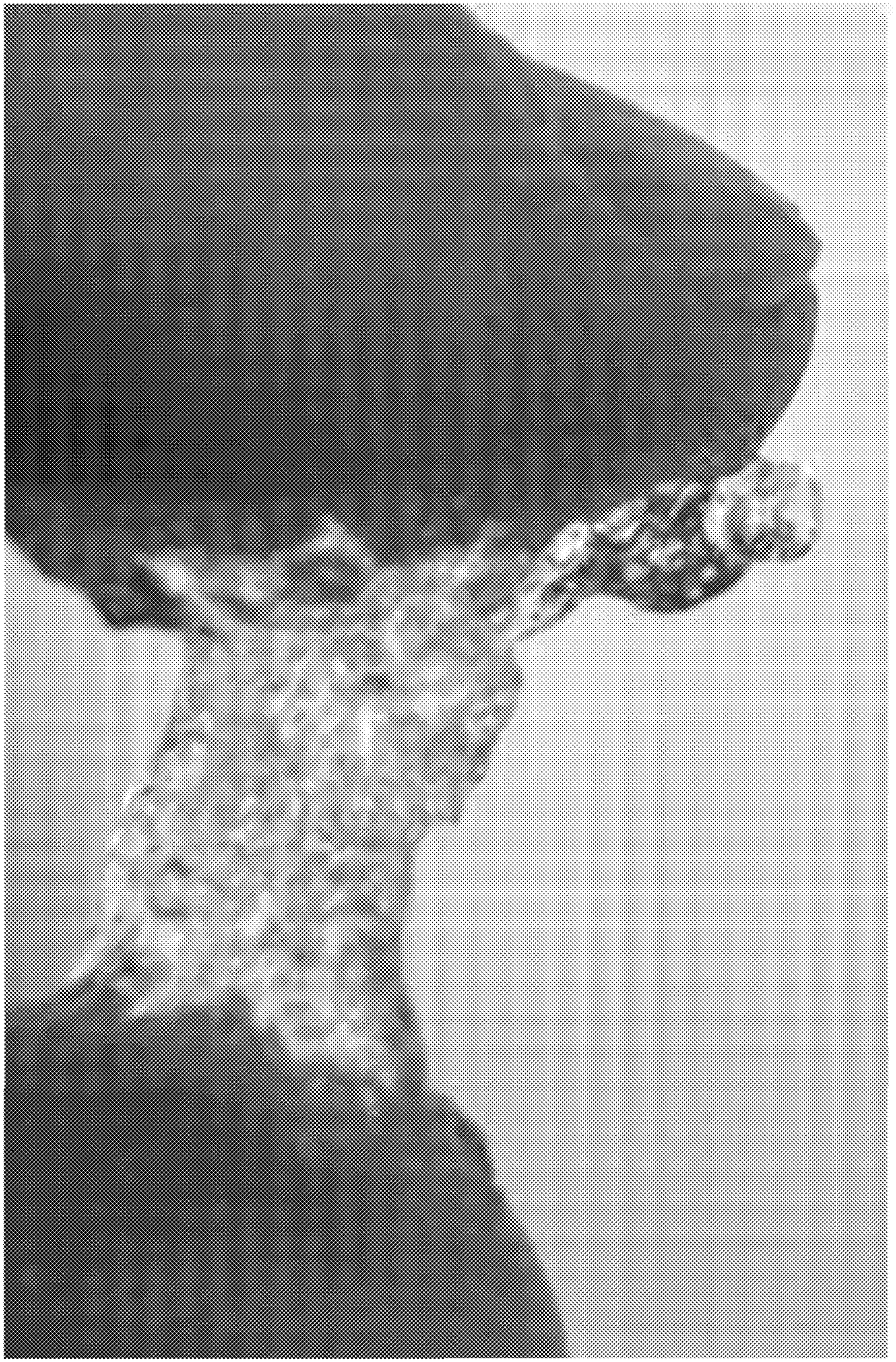

FIG. 4: Carbomer gel: to show the stickiness of the carbomer gel a bit of gel has been taken between two fingers. The fingers then has been spread. As result the gel sticked to the fingers and got thinner in the middle. So it has been show that application was too difficult and the gel is too adhesive.

Figure 5:
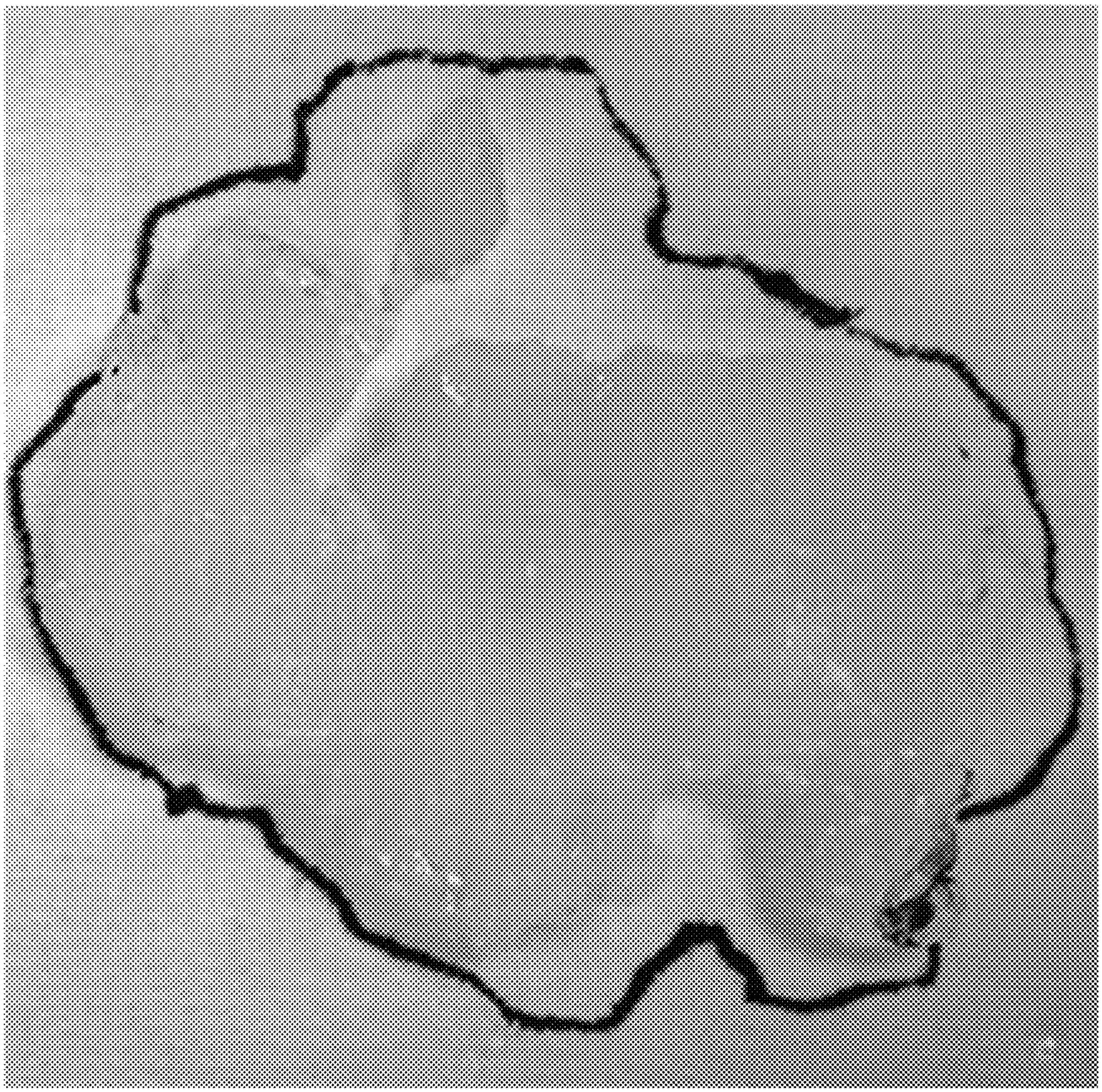

FIG. 5: HEC gel on filter before stored for 24 h at 37° C.: the gel shows a solid character and a good spread-ability/possibility of application at the same time.

Figure 6:

FIG. 6: HEC gel on skin: on skin the application has been tested. The application has been very easy. Moreover a wanted layer of gel has been possible to applicate.

Figure 7:
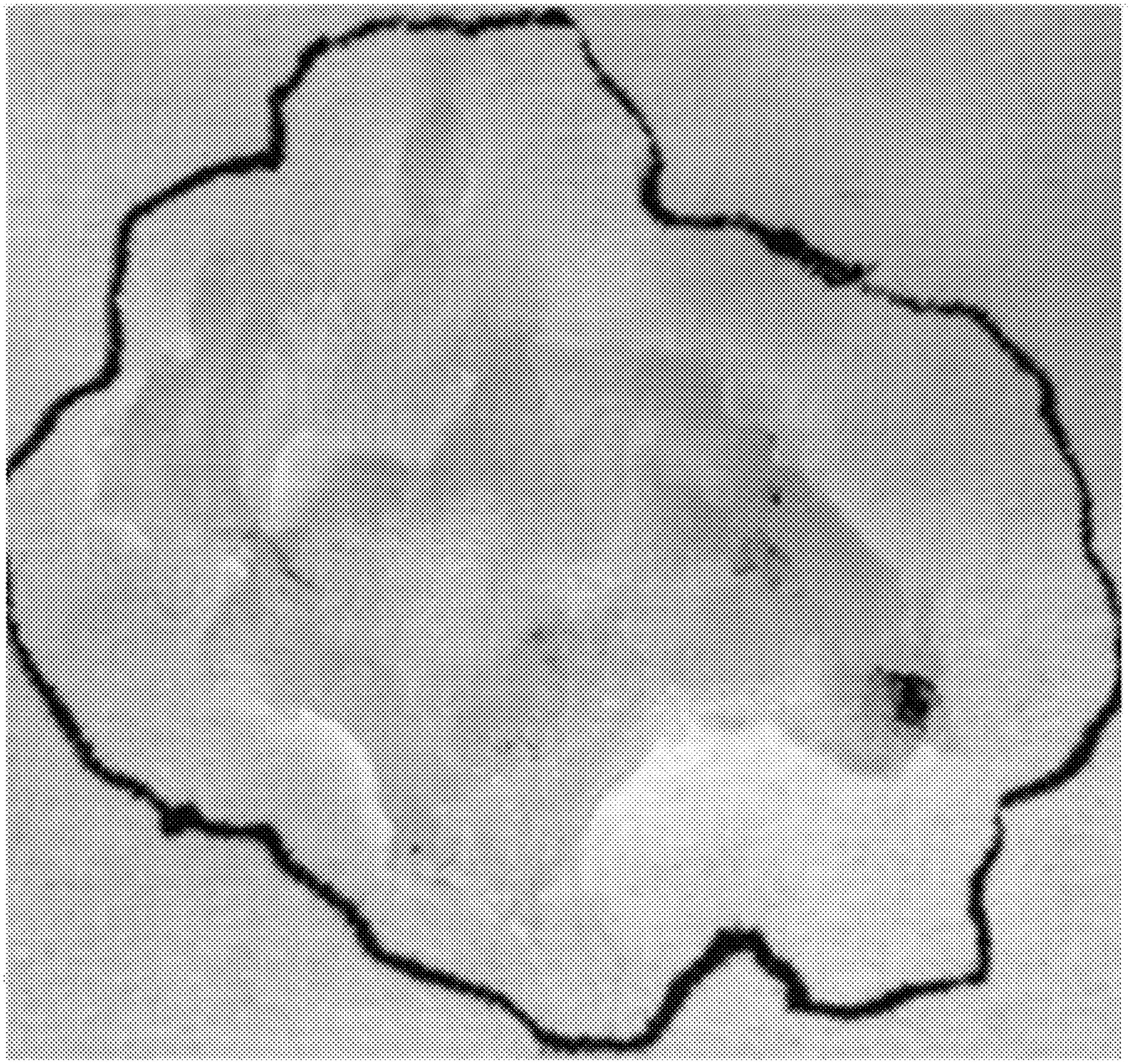

FIG. 7: HEC gel after 24 h at 37° C.: the gel has been dried by the storage-conditions. The solid character after the storage, without any packaging protecting the gel from water evaporation, shows the essential of adequate primary packing. Moreover the gel stayed in the form in which was stored showing an ongoing coverage of the application area.

Figure 8:
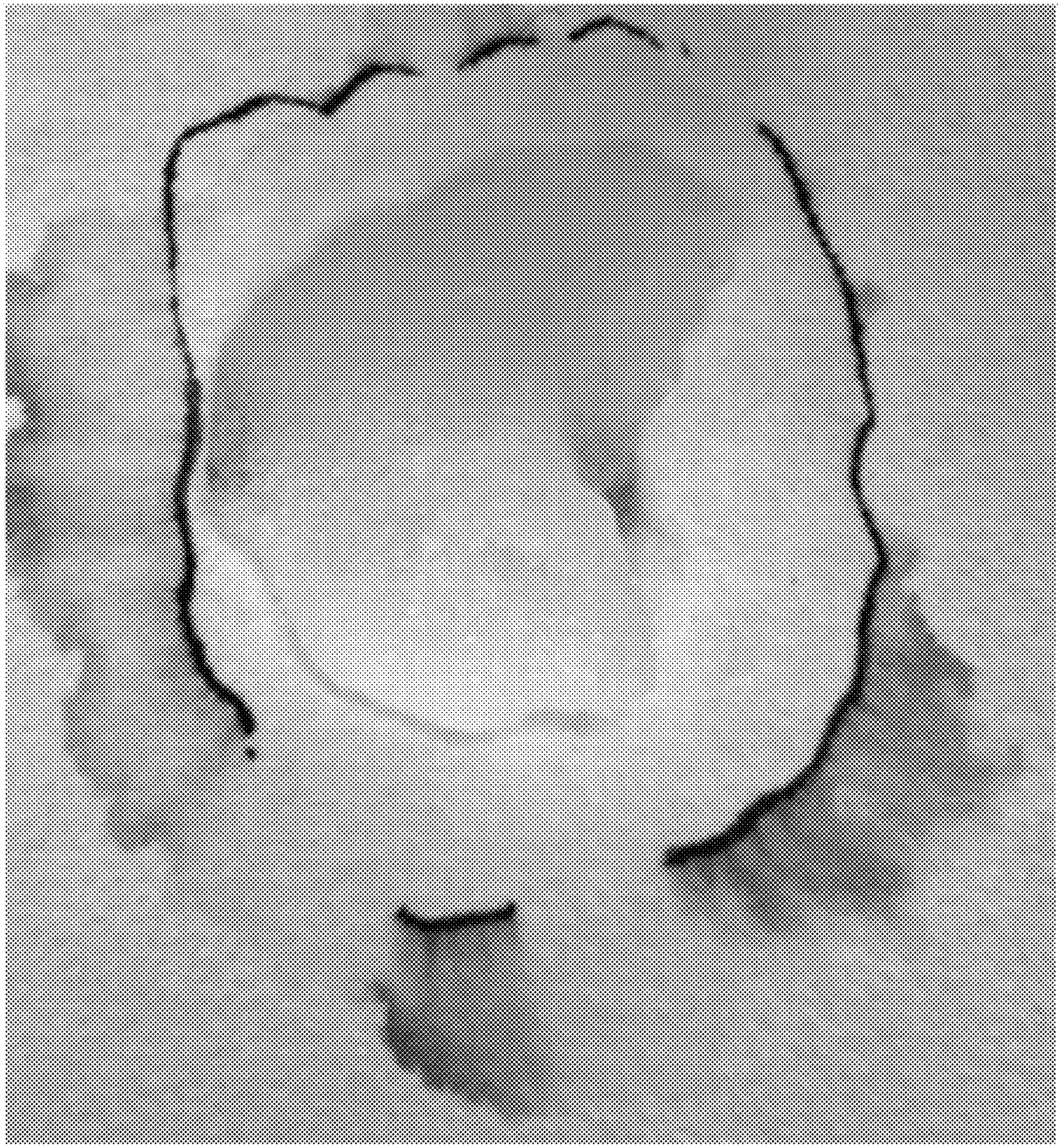

FIG. 8: Polaxamer gel after 24 h at 37° C.; the gel has been dried by the storage-conditions. The solid character after the storage, without any packaging protecting the gel from water evaporation, shows the essential of adequate primary packing. The gel did not stay in the form in which was stored showing a change in the coverage of the application area and a transformation into a cube-like form.

Figure 9:
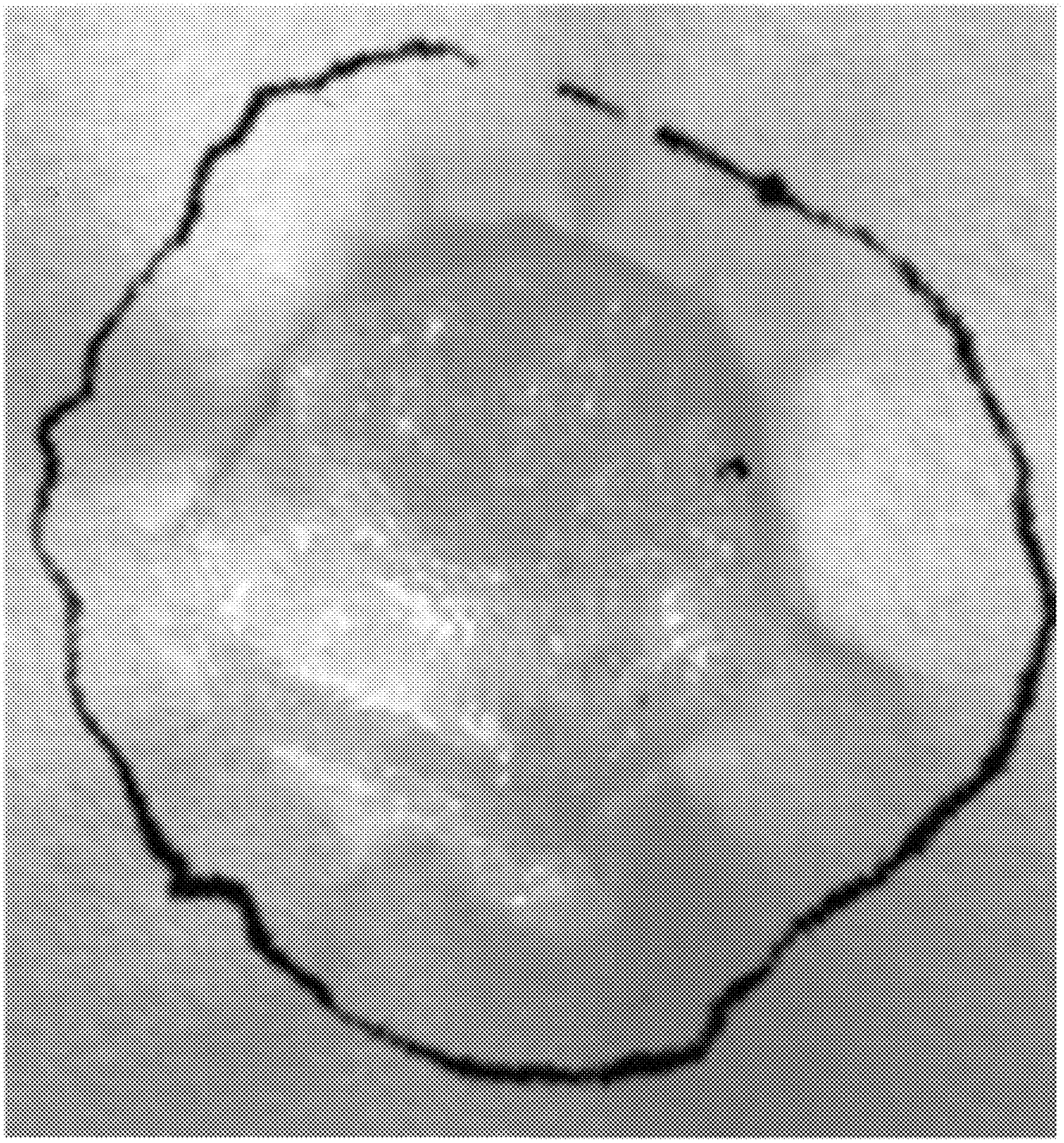

FIG. 9: Na-Hyaluronat gel after 24 h at 37° C.: the gel has been dried by the storage-conditions. The solid character after the storage, without any packaging protecting the gel from water evaporation, shows the essential of adequate primary packing. Moreover the gel did not stay in the form in which was stored showing a change in the coverage of the application area. Stickiness has increased with the loss of water.

Figure 10:

FIG. 10: HEC gel after sterile manufacturing: direct loading method, Ph. Eur. 2.6.1, showing no sign of bacterial contamination after a prolonged testing to increase the probability of detection.

Figure 11:
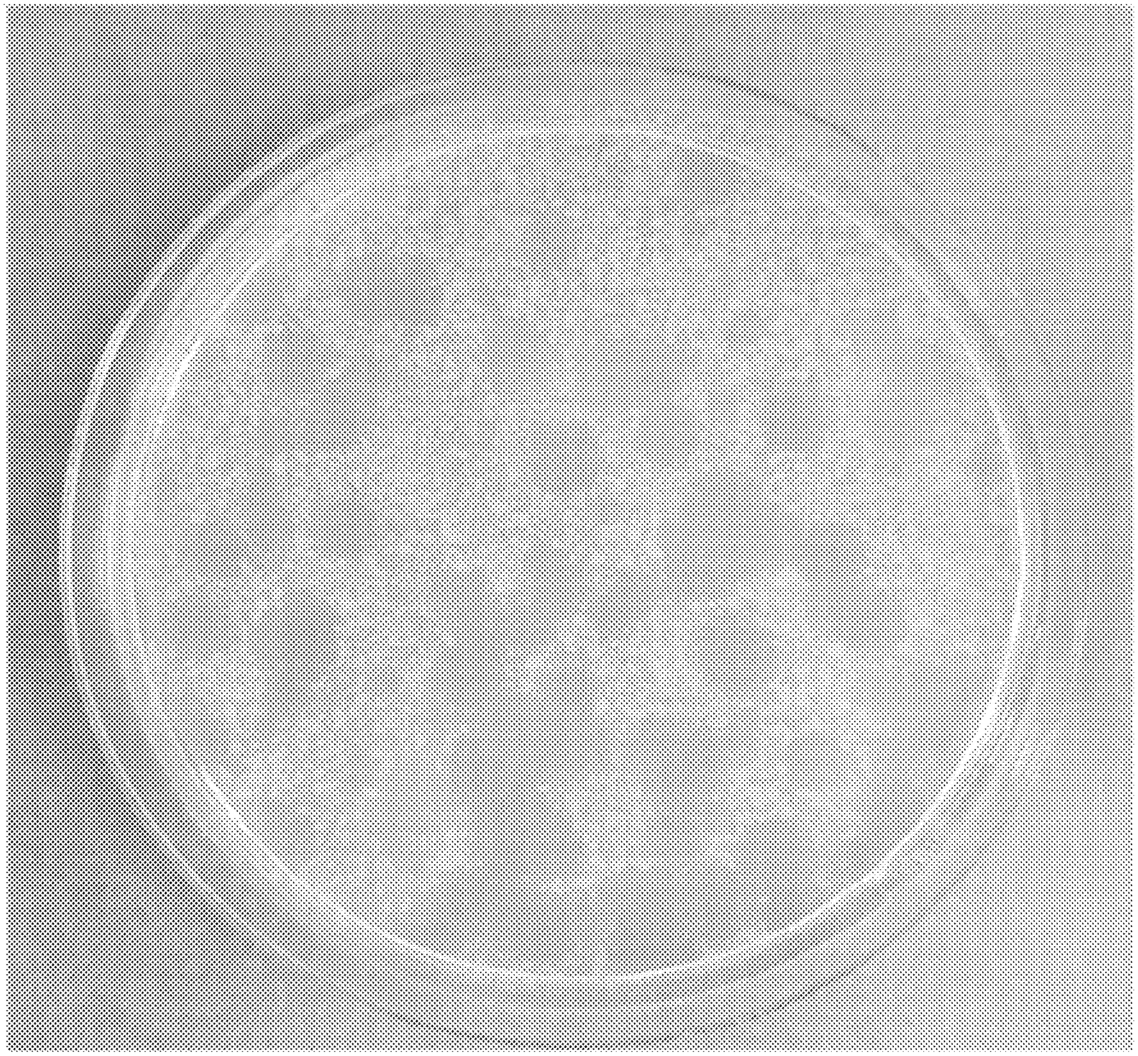

FIG. 11: Plaques could still be detected after steam sterilization of Phages: On a standardized bacterial bio burden phages has been spread out after steam sterilization. After the time of incubation plaques show that phages have survived the steam sterilizing process and are still active.

Figure 12:
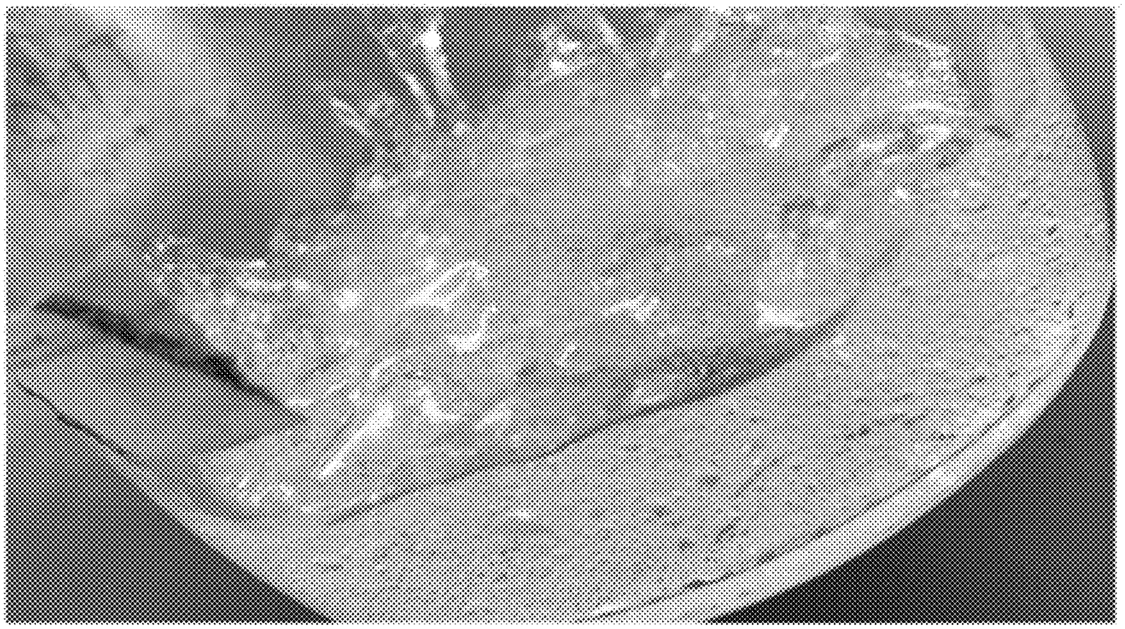

FIG. 12: Sterile preparation of HEC gel: The FIG. 12 shows the sterile result of the combination of phages and gel.

Figure 13:
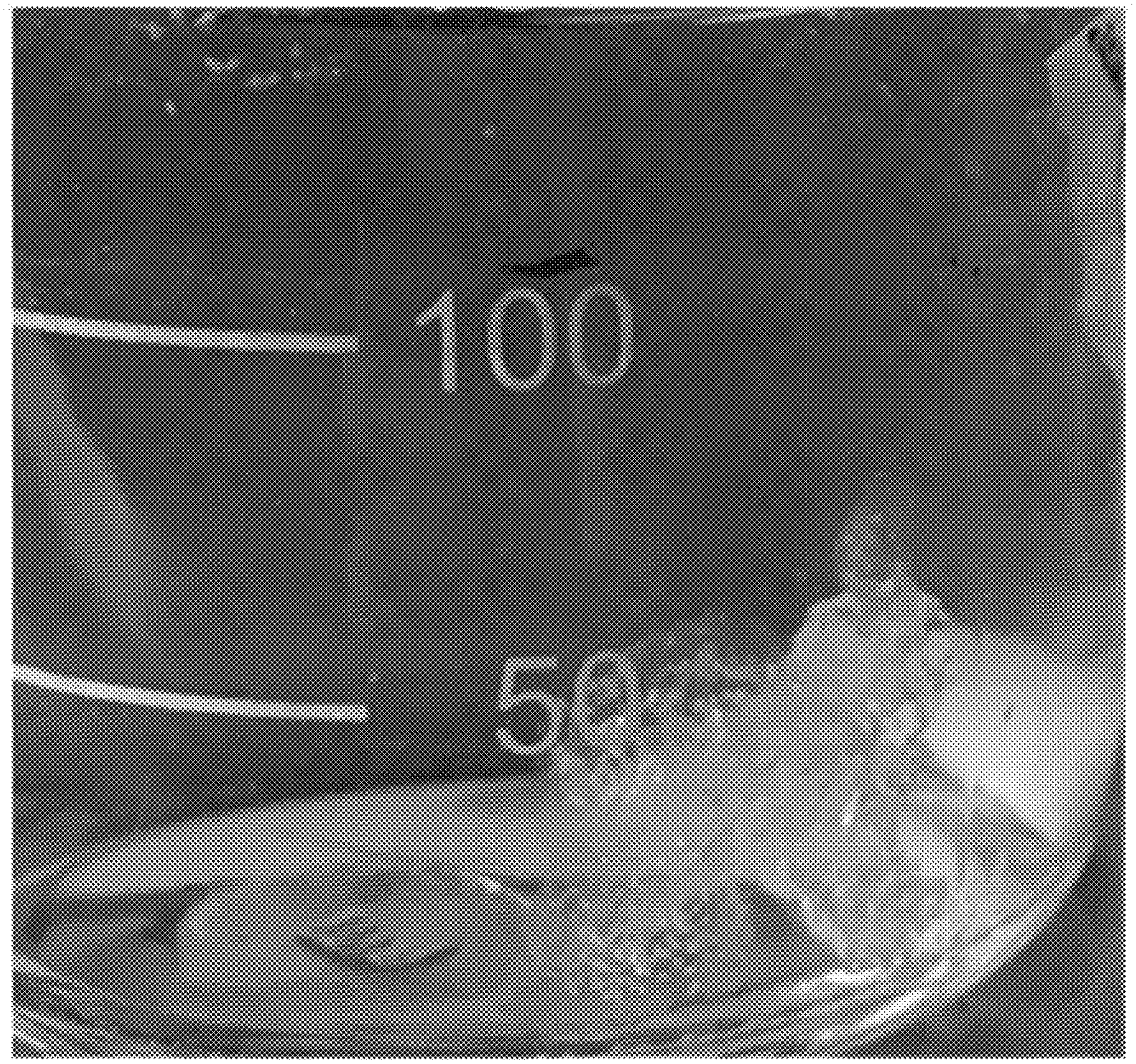

FIG. 13: Gel after steam sterilisation: direct loading method of Ph. Eur 2.6.1, showing no sign of bacterial contamination after a prolonged testing to increase the probability of detection.

Figure 14:
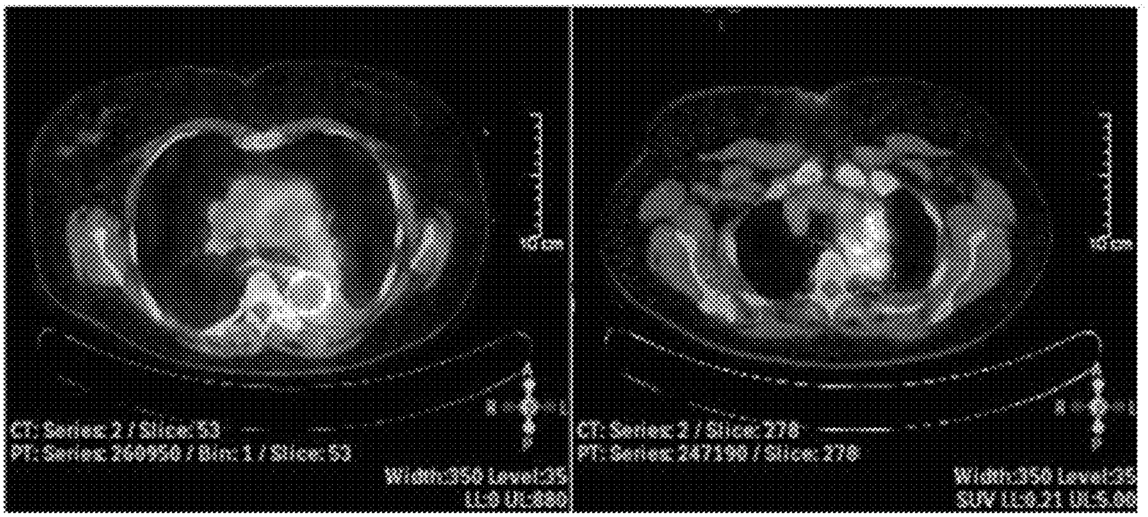

FIG. 14: Preoperative PET-CT. Representative slides from the pre-operative [F18] fluorodeoxyglucose PET-CT scan. The enhancement as the level of accumulation of the tracer substance around the stent-graft in the thoracic aorta is a sign of active inflammation.

Figure 15:
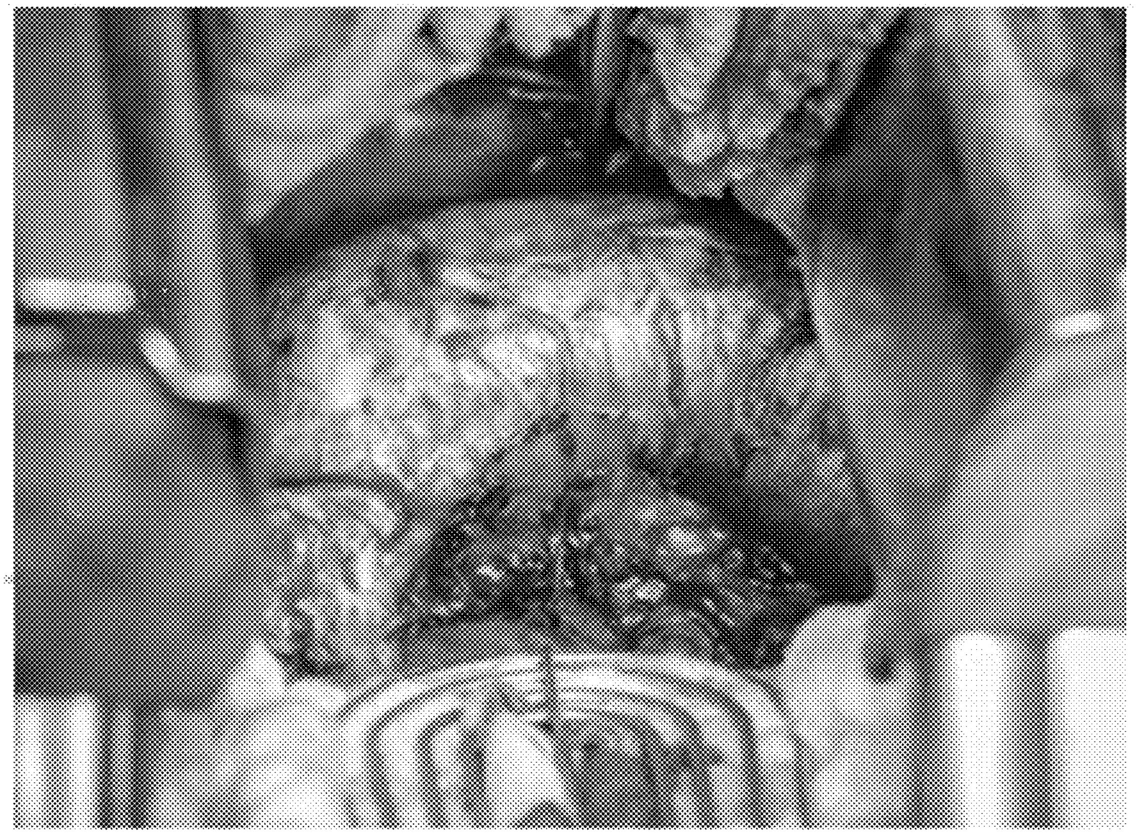

FIG. 15: Intraoperative images from the first step of treatment: The descending aorta has been mechanically debrided from periaortic infectious tissue FIG. 16: Intraoperative images from the first step of treatment: Two endo-sponges had been placed around the aorta.

Figure 17:

FIG. 17: Intraoperative images from the first step of treatment: Finally, another vacuum sponge was applied for ventral coverage of the aorta (C) before the thorax was closed.

Figure 18:
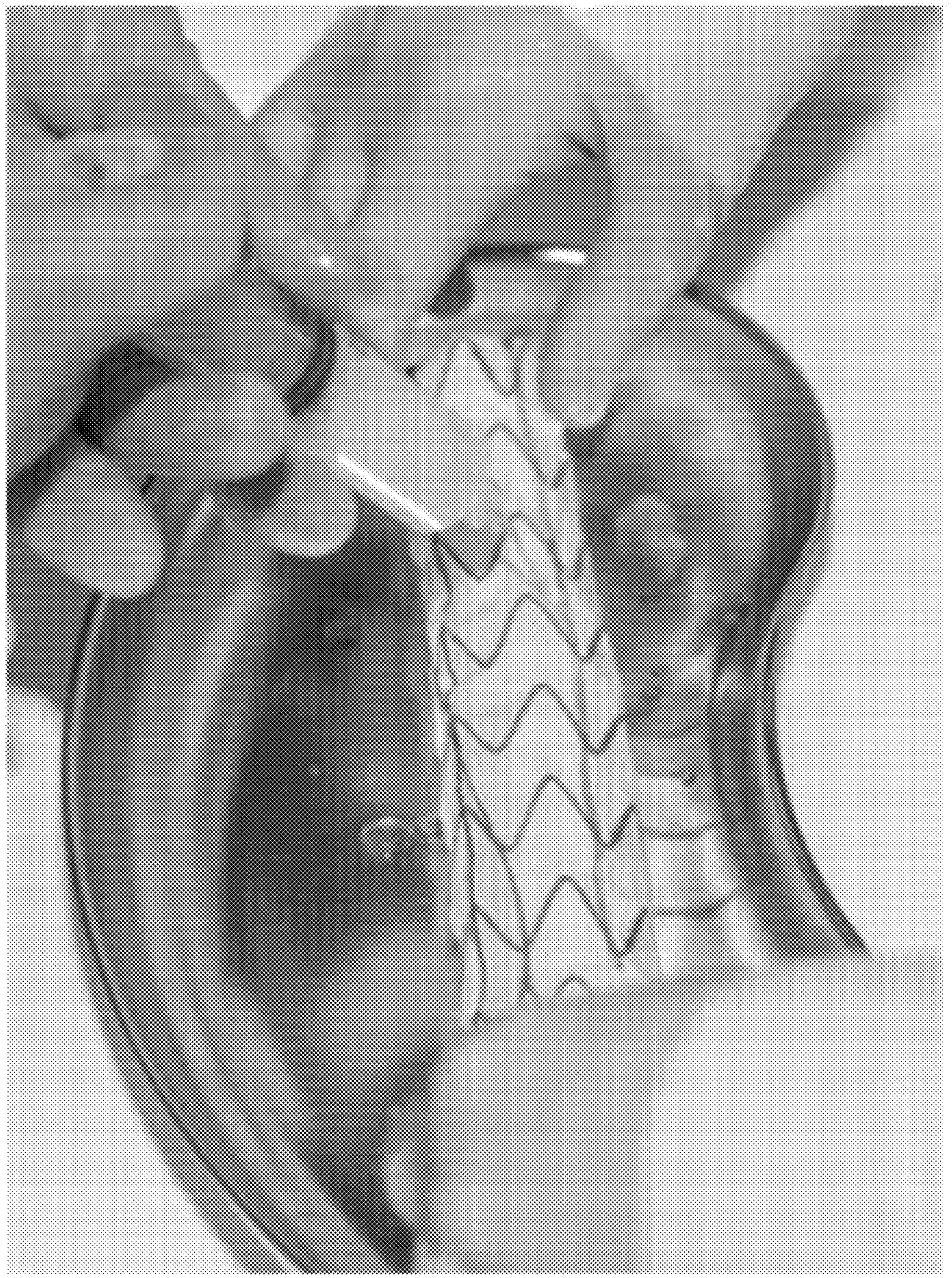

FIG. 18: Off-the-shelf release of an aortic stentgraft system and manual surface covering with bacteriophages gel.

Figure 19:

FIG. 19: Lateral X-Ray after stent implantation, showing a complete overcovering of the infected stent graft by the new ones.

Figure 20:
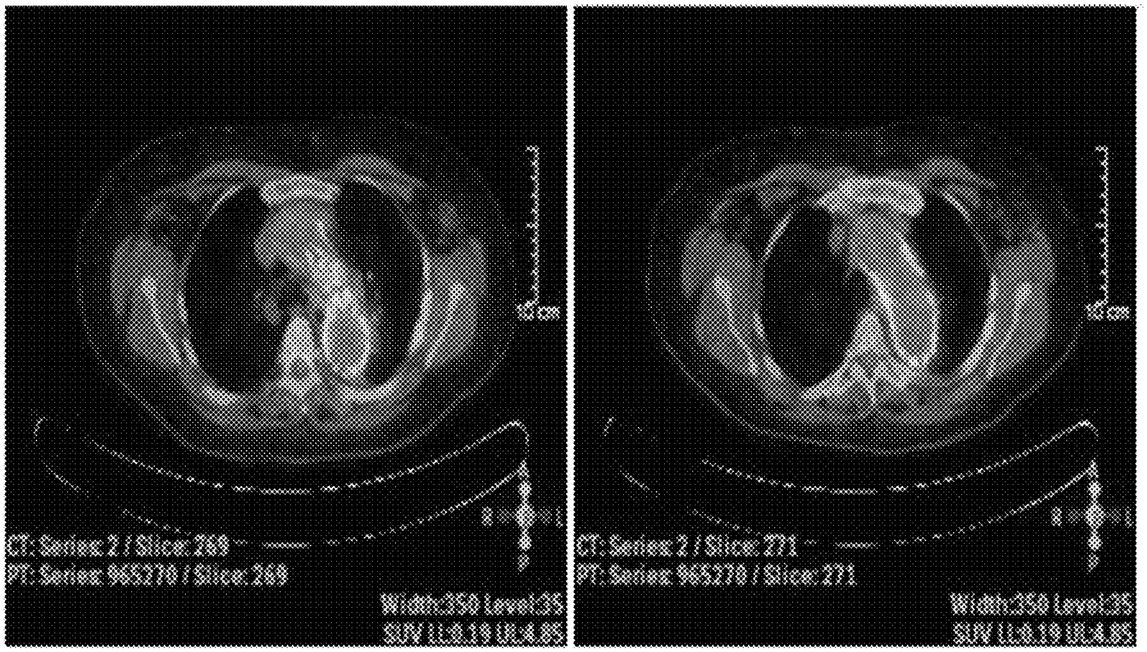

FIG. 20: PET-CT three months after implanting the bacteriophage gel covered stent showing no revealing signs of infection in and around the thoracic aorta.

Figure 21:
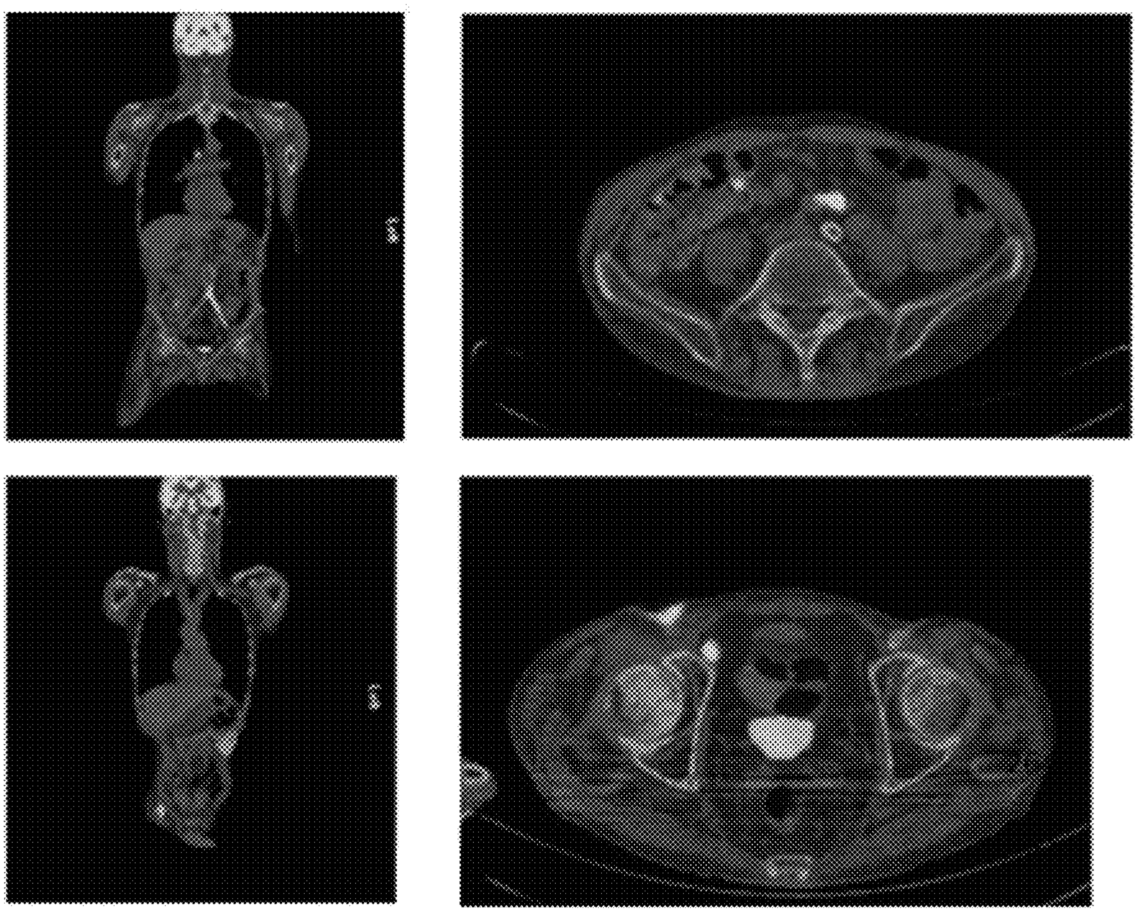

FIG. 21: PET-CT showing the infected aortic-bi-femoral vascular graft with right femoral tissue infection.

Figure 22:
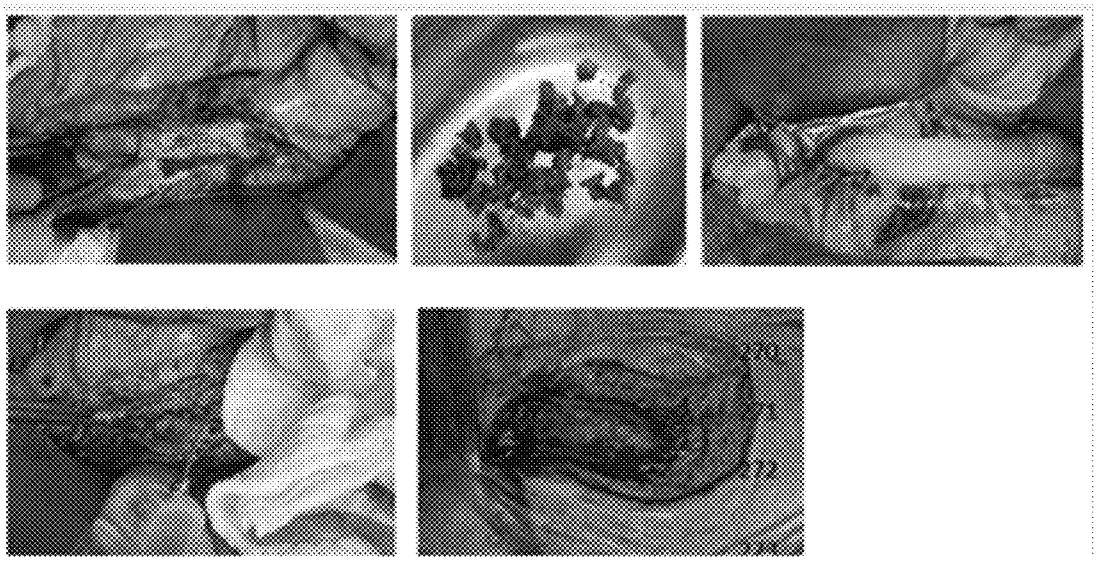
Figure 23:
Figure 24:
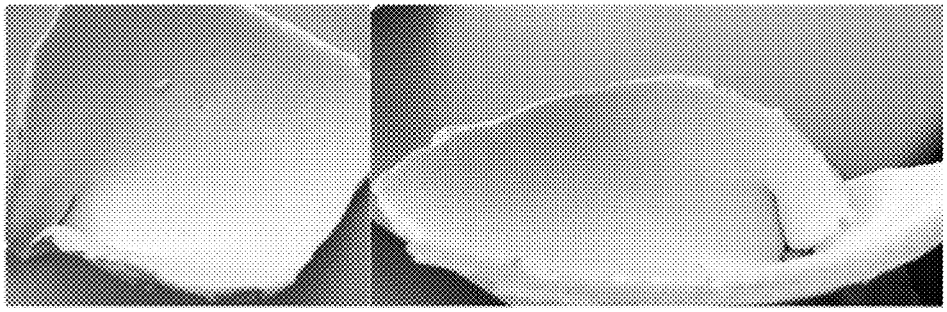

FIG. 22: Impressions of the surgical procedures and the application of the bacteriophages gel FIG. 23: PET-CT three months post intervention without signs of infection enclosing the aorta or both femoral regions FIG. 24: Exemplary pictures of lyophilized hydrogels.

Figure 25:
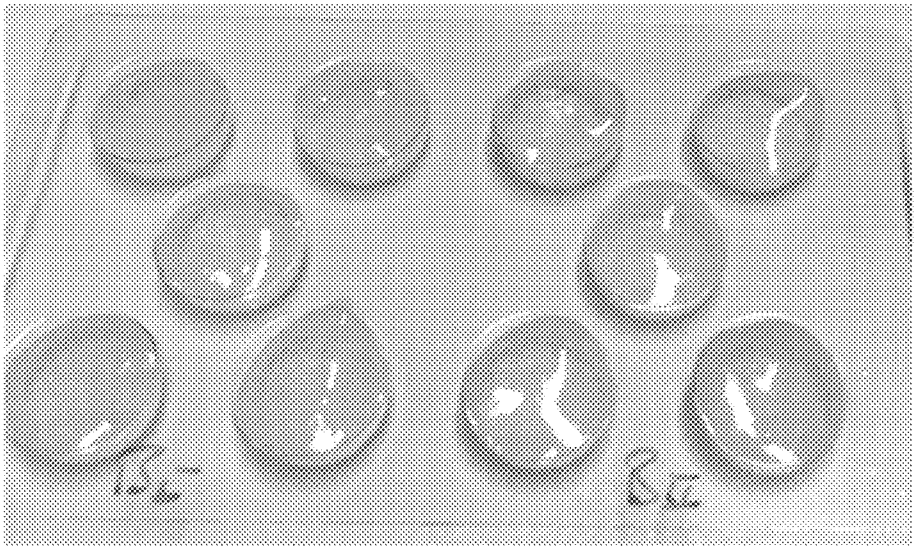

FIG. 25: Preparation of lyophilizates from bacteriophage comprising hydrogels.

Figure 26:
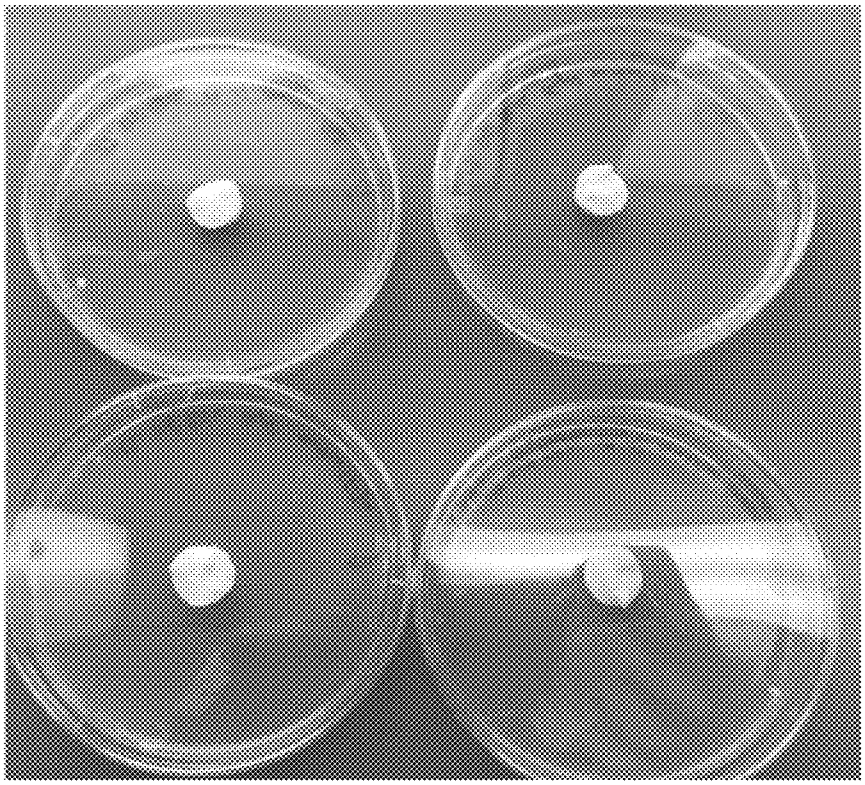

FIG. 26: Four lyophilizated hydrogels centered on agar plates with *Staphylococcus aureus.*

Figure 27:
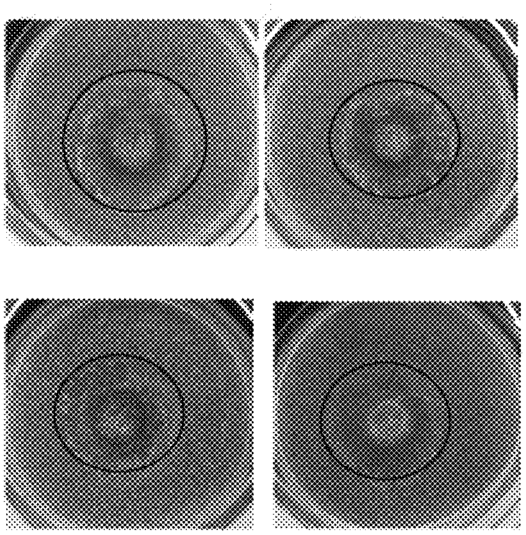

FIG. 27: Bacteria-free (circled) plaques on the culture medium.

Figure 28:

FIG. 28: Experimental setup.

Figure 29:
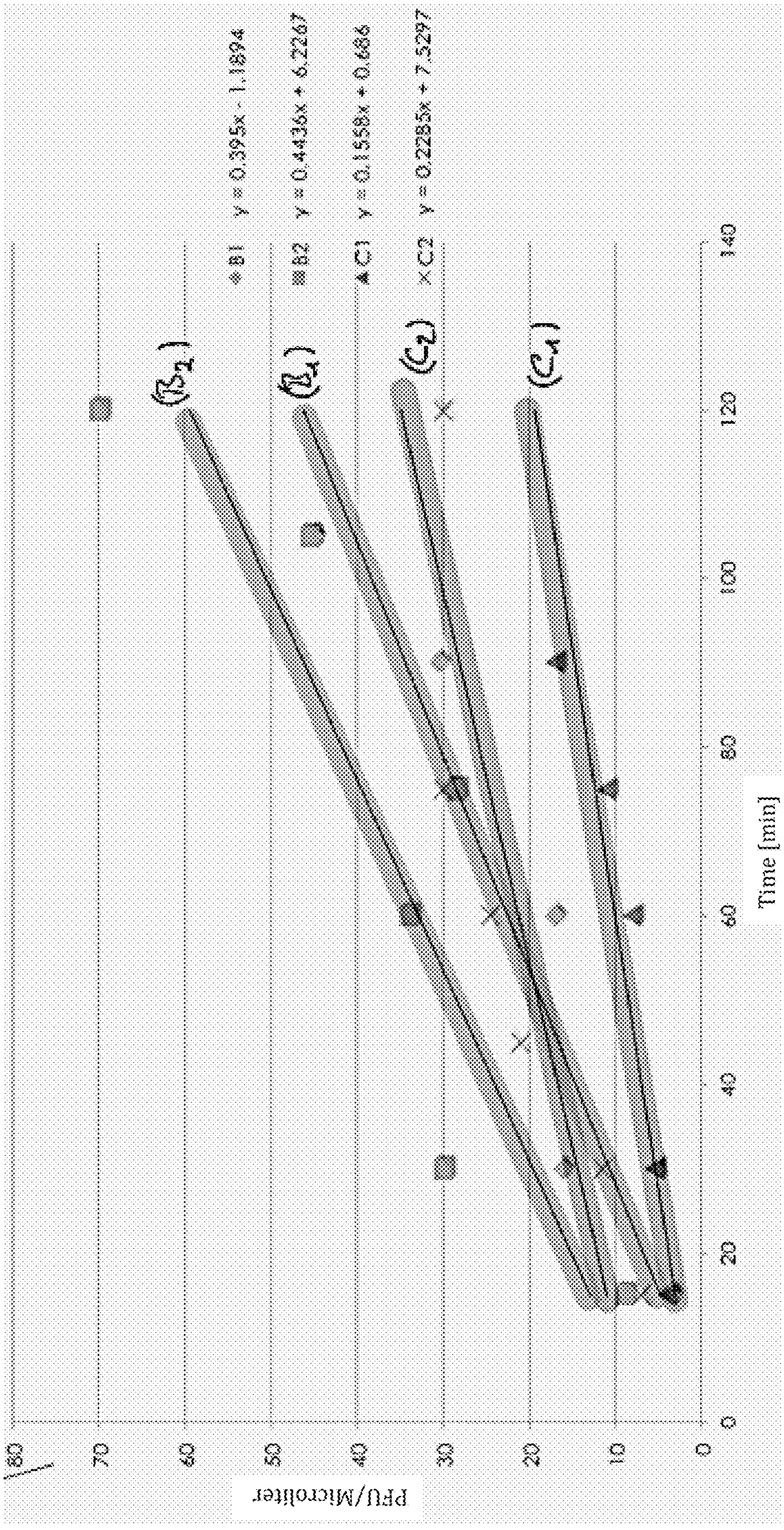

FIG. 29: Data of release of bacteriophages from the products B1, B2, C1 and C2 over time of Example 5: x-axis showing bacteriophage (BPh) concentration in [pfu/ml] and y-axis showing time in [min].

Figure 30:

FIG. 30: Hurley II/III in left axilla (left picture) and Hurley II/III right gluteal (right picture).

Figure 31:
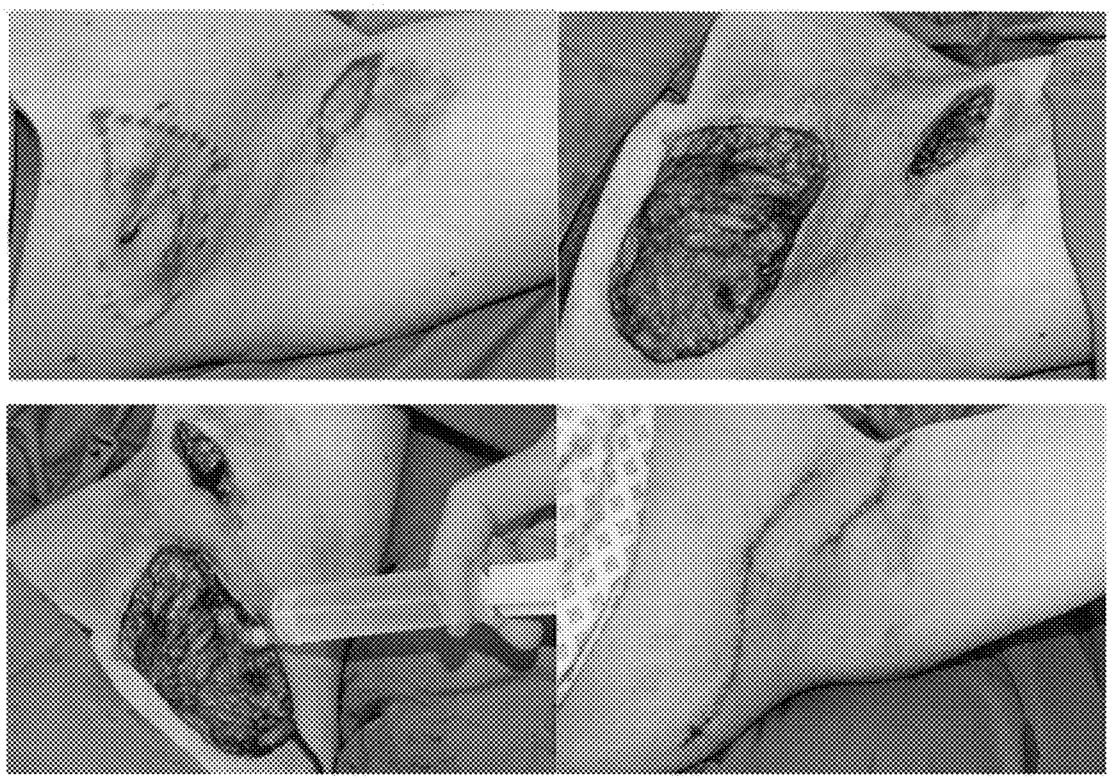

FIG. 31: Surgical treatment of the left axilla comprising administration of a hydrogel comprising HEC and bacteriophages. First, the left axilla received local anaesthesia (top left) followed by surgical removal of the affected tissue (surgical access left axilla, top right), bacteriophage and carrier application (bottom left) and subsequent skin suture of the axilla (bottom right).

Figure 32:
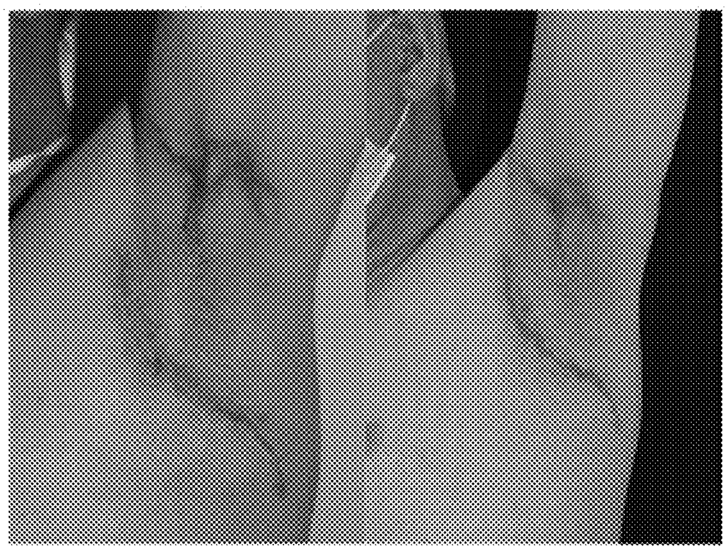

FIG. 32: Axilla status after 2 weeks (left) and 10 weeks (right).

Figure 33:

FIG. 33: Gluteal status after 2 weeks (top) and 10 weeks (bottom).

Figure 34:
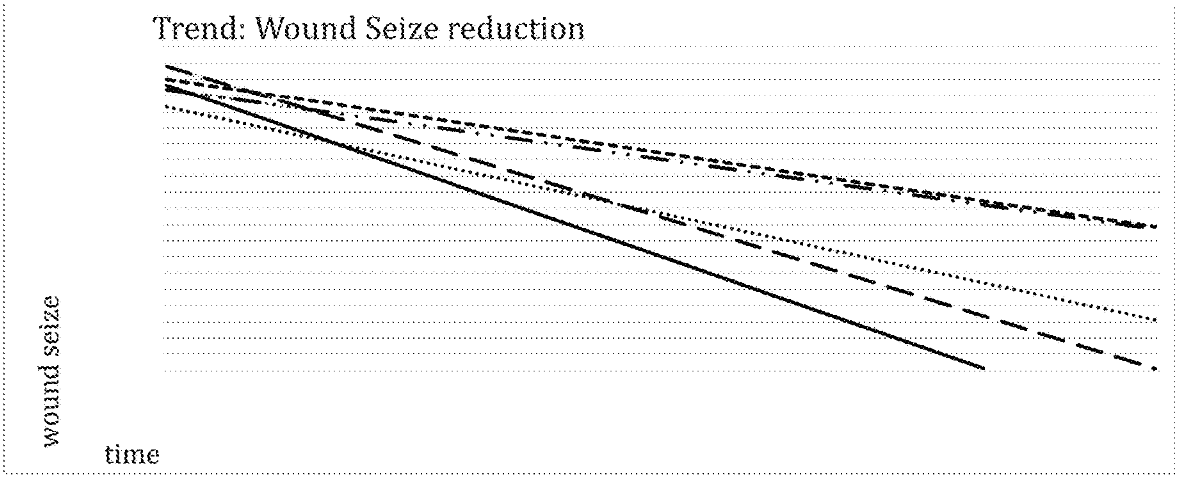

FIG. 34: Wound seize reduction over time with the x-axis showing the time and the y-axis indicating wound seize.

EXAMPLE 1

Finding a Suitable Phage Containing Gel—Galenic for Clinical Use: A Laboratory Trail Abstract In vitro laboratory tests were carried out to find a suitable basis-gel for the PhaTEC Phages Gel-Product. The shortlist of gel formers included Hydroxy-Ethyl-Cellulose (=HEC), Sodium-Hyaluronate, Polaxamer, Carbomer and Silicon dioxide (=$SiO_2$ [highly dispersed]). Testing was performed according to spreadability on filter paper and on the skin, the haptics and sensory properties, as well as the gel consistency and the behavior after 24 h at 37° C. As bacteriophages we used a cocktail of different Bacteriophages (SniPha 360) which can be purchased from the company "Phage24" in Austria. The requirements are placed on the gel, which is to become the subsequent basis of the PhaTEC Product. All tests were carried out under sterile conditions in the laboratory of Pohl-Boskamp GmbH & Co. KG, taking GLP (good laboratory practice) into account.

With regard to sterilization, in our experiments various methods are shown that lead to a sterile product of the HEC gel and the phage cocktail.

Furthermore, both the HEC gel and the phages can be steam sterilized. Thus, the PhaTEC product, containing the gel and phages, can be sterilized in the final container for easy and cost-effective industrial production.

1. BACKGROUND

1. Stability and Spreadability

The PhaTEC product is to be used for intra- and extra-corporal application. Among other things, the product is to be applied to mucous and skin areas, wounds and surgical sites such as anastomoses. For this purpose, an appropriate spreadability is required (to cover an application area) with simultaneous product stability—for example, to generate/apply an individual layer thickness and to remain at the place of application. Moreover, the gel should be spreadable so that it can be applied easily and painlessly to sensitive areas such as fresh wounds. In addition, cooling is desirable, especially in the case of extra-corporeal application, in order to counteract inflammatory reactions and to provide a pleasant feeling on the application area.

2. Possibility of Sterilization

Due to the pursuit of a product that is intended for extra- as well as intra-corporeal application, the product and thus the initial components, such as the base gel, have to provide the possibility of sterility.

3. Adequate Spreading Around the Place of Application

The gel should be reduced in viscosity by the introduction of skin or body temperature and body water, so that the phages contained later are released over a defined time. This results in a prolonged release of the therapeutic agent, which does not affect the body, due to the degradation of the product by dilution and physiological excretion processes.

4. Feeling on the Skin

To all medical, as well as pharmaceutical requirements, the acceptance of the patient is essential. Since the phages do not cause any physical reactions and have no side effects, the gel, which the patient feels, especially when applied cutaneous/extra-corporal, must be pleasant on the skin and/or mucous membrane.

2. Gel-Manufacturing

Initially, all gels were prepared with a gel former content of 13%. The Carbomer, Na-hyaluronate and HEC gels were the easiest to prepare.

From the Five Preparations, Only Three Solid Gels were Obtained:

HEC-, Carbomer- and Sodium hyaluronate-Gel. The Silicon dioxide—at the applied concentration—formed a viscous liquid but not a solid gel and did not dissolve completely. The Polaxamer showed gel-islands that were not connected with each other; in addition, much water was not absorbed (FIG. 1)

3. Haptic/Sensory Skin Testing

Methods:

Different Gel-formations had been tested at the skin surface of the same test person. Sensitive feeling as far as skin reaction had been observed.

The Na-hyaluronate (Natriumhyaluronat EP) gel was much too firm to be spread well on the filter paper. FIG. 1

On the skin, especially on hairy skin areas such as the arm used in the test, application and spreading was painful, due to the firm condition. FIG. 2

The Carbomer (Carbomer EP; Carboprol 71 G) gel was highly adhesive and therefore difficult to spread on the filter paper and almost impossible to spread on the skin. Moreover, on the skin, especially on hairy skin areas such as the arm used in the test, application and spreading was painful, due to the stickiness: FIG. 3, FIG. 4

The HEC (Natrosol 250 HX) gel felt the most pleasant: It was easily spreadable on the filter paper and on the skin with a simultaneous firmness that allowed application of individual layer thicknesses: FIG. 5, FIG. 6

Results:

The feeling of the gels proved to be very different: The gels showed very different characteristics: If the $SiO_2$ (hochdisperses Siliciumdioxid; Aeroperl 300 Pharma) and Polaxamer (Polaxamer 407) gel were not tested on the filter paper and/or skin due to the liquid state of the $SiO_2$ gel and due to the island formation of the Polaxamer gel, the Carbomer gel was found to be highly adhesive and difficult to apply because of the free flowing properties. The stickiness of the Carbomer gel was very unpleasant when applied to the skin and painful in hairy areas, such as (in the test) the arm. The cooling effect was almost immediately noticeable. The gel, especially on the skin, did not remain at the application site and immediately flowed undirected and uncontrolled into the surrounding area. An appropriate layer thickness could not be applied.

The Sodium hyaluronate gel was much too firm for painless, simple application: It could hardly be spread on the filter paper and on the skin, especially in hairy areas, such as (in the test) the arm, it was painful and difficult to spread due to its firmness.

Hard, but still easy and painless to apply and remaining at the application site as desired, was the HEC gel: Here, it was not only possible to demonstrate good spreadability on the filter paper and on the skin; the feeling on the skin was also pleasant. Application on the skin was simple and painless. The gel distribution could be done individually with regard to the desired layer thickness. The cooling effect occurred after some time due to the applied layer thickness. In addition, the applied gel layer gave a feeling of a protective layer, like a plaster or similar.

4. Gel-Galenic Behavior Under Drying Conditions

The heat exposure of 37° C. was carried out by means of a drying oven. In order to test the cooling effect desired when external applied, the gels (10 ml each) were placed in the center of a filter paper and the border was marked. The gels were stored at 37° C. for 24 h in order to demonstrate the drying of the gels and thus a cooling effect due to evaporative cooling.

Methods:

The haptic/sensory test after 24 h at 37° C. was performed with gels that were in cups with the lid on in the drying cabinet. FIG. 7, FIG. 8, FIG. 9

Results:

The primary packaging provided adequate protection against dehydration. Under physiological conditions, the product is liquefied by the interstitial water and physiologically degraded.

5. Sterility 5.1. Sterile Production 5.1.1. Gel

Methods:

The gel was sterilely prepared in laboratory-scale tests. For this purpose, previously sterilized equipment and a Bench (laminar air flow) were used. The prepared HEC gel was tested according to the direct loading method of Ph. Eur 2.6.1. (FIG. 5).

Results:

No bacterial growth after 24 h until 9 days, when the extended test was ended. No microbial growth was evident over the entire period. FIG. 10

5.1.2. Phages

It is a defined objective of PhaTEC that its phage products can be produced industrially, standardized and easily. A major aspect of a simple, industrial production is the sterilization of the product in the final container. Two possibilities of sterilization of the gel are described above and have been verified by the corresponding tests. The phages can be sterilized via sterile filtration, as tested and described earlier.

Methods:

Phages were sterile-filtered and showed no bacterial growth on different culture media after 24, 48 and 72 h at 37° C. The cocktail was tested positive on an *E. coli* bacteria culture on agar, Samples of the phage cocktail, containing about $10^7$ pfu/ml, were steam sterilized and carried out the test with the steam sterilized BPG against the same bacterial strain on fresh corresponding agar.

Results:

Plaques could be detected, approx. 6×10^2 PFU/ml. That leads to the result, that steam-sterilized bacteriophages from our phage cocktail still have lytic activity against the corresponding bacterial strain. FIG. 11

In conclusion it has been demonstrated, that Steam-sterilization of phages is possible.

5.2. Steam Sterilization 5.2.1. Gel

Methods:

The gel was prepared, in addition to sterile manufacture, in a normal laboratory clean setting and steam sterilized in the final container. FIG. 12

Results:

The steam sterilized HEC gel showed no growth over the entire time when tested as described under "Sterile Preparation". FIG. 13

6. Summary

Among the most suitable gel formers tested, Hydroxy-Ethyl-Cellulose is the best gel former: the haptic, the good, uniform, even protective feel on the skin, as well as the properties of easy application, also in terms of a desired layer thickness, are just some of the aspects that lead to this result.

With regard to sterilization, there are various methods shown that lead to a sterile product of the HEC gel and the phage cocktail. All individual tests lead to the conclusion that all methods and procedures, presented above, are suitable to bring the PhaTEC Product into a sterile state.

Furthermore, both the HEC gel and the phages can be steam sterilized. Thus, the PhaTEC product, containing the gel and phages, can be sterilized in the final container for easy and cost-effective industrial production.

EXAMPLE 2

Successful Treatment of an Infected TEVAR with Extra- and Endovascular Bacteriophage Application Abstract Objectives: Graft infections are severe complications in vascular surgery. Surgical resection of infected aortic stent-grafts is associated with high mortality and morbidity. Therefore, alternatives to inadequate antibiotic treatment and extensive surgery are urgently needed.

Case

A 67-years-old woman was admitted with an infected stent-graft in the thoracic aorta. Local infection was confirmed by PET-CT imaging. Due to comorbidities, surgical resection of the stent-graft was not feasible. Therefore, a three-step approach for local bacteriophage treatment was performed as a last-resort treatment. First, the para-aortic tissue was debrided via left thoracotomy, a bacteriophage suspension was applied around the aorta and an irrigation-vacuum-system was installed. After repeated alternating instillation of the bacteriophage suspension for three days, as the second step vacuum sponges were removed and a bacteriophage-containing gel was locally applied locally around the aorta. In the third step, the bacteriophage-containing gel was applied to a thoracic stent-graft, which in turn was endovascularly placed into the infected stent. After 28 days, the patient was discharged from hospital with normalized infection parameters. PET-CT imaging at three months post intervention did not show signs of infection in or around the thoracic aorta.

Conclusions:

This case demonstrates successful treatment of an infected endovascular stent-graft by application of bacteriophages both to extravascular and, as a novel approach, endovascular sites using a bacteriophage-coated stent-graft. This success was only possible due to the hydrogel comprising HEC and bacteriophages according to the first aspect of the present invention, which allowed localization of phages in situ at the site of infection as well as continuous bacteriophage release in a retarded manner.

Keywords:

*Staphylococcus aureus* sepsis, graft infection, phage therapy, antibiotic resistance Background In vascular surgery, infections of vascular grafts are severe complications. Especially infections of endovascular aortic stent-grafts are associated with a high morbidity and mortality up to 75%. Since these endovascular procedures are often performed in older patients with multiple comorbidities who do not qualify for open aortic repair, the required removal of the infected stent-grafts and in situ reconstruction with autologous tissue or extra-anatomic replacement are related with early postoperative morbidity and mortality over 20%. Even with successful treatment, the reinfection rate is up to 20%.

Bacteria embedded into the peri-prosthetic tissue form a surface-adherent biofilm and therefore have a up to 1000-fold greater tolerance to antibiotics. Vice versa, even targeted antibiotic treatment can only suppress a stent-graft infection and is no curative treatment option.

In order to reduce the morbidity and mortality of the unavoidable surgical treatment, alternative less invasive approaches are urgently needed. In this context, bacteriophages and their bacteriolytic activities are a promising therapeutic option.

Case

In August 2020, a 67-year-old female patient was admitted to the hospital due to worsening general condition and thoracic respiratory pain. There was a pronounced cough with deep inspiration, without sputum, and fever up to 38.6° C. Infection with Sars-CoV-2 was ruled out. The patient showed a leukocyte count of $16.7\times10^9$/l and a serum C-reactive protein value of 199.6 mg/l. Secondary findings included a condition after thoracoabdominal stent graft implantation (COOK stent 34/152 mm) after Stanford type-B aortic dissection in February 2009. Furthermore, the patient suffered from Osler disease that required prednisolone treatment, condition after lung artery embolism, arterial hypertension, an atrophic left kidney and diverticulosis of the sigmoid colon.

Chest X-ray showed no evidence of pneumonia. Antibiotic therapy with ampicillin/sulbactam and roxithromycin was started. After *Staphylococcus aureus* was detected in the blood culture, antibiotic therapy was switched to Flucloxacillin and after five days, to cefuroxime due to an allergic skin eczema.

Endocarditis was ruled out. The patient showed progression of known leukocytoclastic vasculitis with involvement of both legs, arms, cleavage, hands, and soles without involving the kidneys. Cutaneous symptoms improved with intense prednisolone therapy. The progression of vasculitis was considered a reaction to the systemic infection. The antibiotic treatment was switched to meropenem and cefazolin.

A computed tomography scan of the chest and abdomen did not reveal infection foci. To rule out the aortic stent graft as a focus of infection, a fluorodeoxyglucose PET-CT was performed.

As a result, pathologically increased metabolic activity of the entire proximal aortic stent was visualized, beginning at the level of the mid-aortic arch and extending to the level of the eighth thoracic vertebra as a sign of florid stent infection. Additionally, inflammatory mediastinal soft tissue swelling and left pleural effusion were described. FIG. 14.

Due to the bad condition and several comorbidities of the patient, the surgical resection of the infected stent-graft and autologous anatomical reconstruction were not feasible. The patient herself whished an alternative to indefinite systemical antibacterial treatment. Therefore, an experimental approach using local bacteriophage application was planned as a last resort treatment according to Article 37 of the Declaration of Helsinki in accordance with the local ethics committee (A 2021-0132).

Bacteriophage Treatment

As a curative therapeutic strategy a three-step approach for both extra- and endovascular application of SniPha 360 (Phage24.com, Austria) was performed. SniPha 360 is a commercially available cocktail of lytic bacteriophages against *Escherichia coli, Staphylococcus aureus, Pseudomonas aeruginosa, Streptococcus pyogenes, Proteus vulgaris* and *Proteus mirabilis.*

After the risks and benefits of the experimental procedure were explained, the patient consented to the therapy. First, the extravascular treatment was performed by left-sided thoracotomy. The visceral pleura was found to adhere to the aorta. After obtaining local swab specimens for microbiological analysis, debridement and jet-lavage were performed. Then, 20 ml SniPha 360, diluted in 100 ml 0.9% NaCl were dropwise applied onto the infected para-aortic tissue. Then, two endo-sponges (Endo-SPONGE®, B. Braun, Melsungen, Germany) were placed on the small and large curvature of the aortic arch and the proximal descending aorta respectively, followed by a V.A.C.® GRANFOAM™ Dressing sponge (18×12.5×3.2 cm, KCl Medizinprodukte GmbH, Wiesbaden, Germany) (FIG. 2C). The endo-sponges were connected to the V.A.C. VERAFLO™ Therapy system (KCl Medizinprodukte GmbH). To avoid contact of the sponges to the lunge a Suprasorb® CNP Drainage film (25×20 cm, Lohman-Rauscher GmbH & Co., Neuwied, Germany) was placed above the sponges. The thorax was closed after placing a chest tube and the patient was referred to intermediate care unit.

Figure 16:

There, once daily, the intrathoracic fluid was pumped out via the V.A.C. VERAFLO™ therapy system two hours prior bacteriophage treatment, followed by three times flushing and draining of the sponges with 500 ml 0.9% NaCl, respectively. Afterwards, the endo-sponges were flushed with 20 ml SniPha 360, diluted in 100 ml 0.9% NaCl. Both the endo-sponges drainage and the chest tube were clamped until the next day. FIG. 15, FIG. 16, FIG. 17

As the second step, the patient was re-thoracotomized after three days. After extraction of all vacuum sponges, the aorta and its surrounding tissue were covered with 40 ml SniPha 360 incorporated in 15.8% hydroxyethylcellulose gel. The thorax was closed and the patient was transferred to intermediate care unit.

The third step was performed after another three days. Therefore, two sterile RELAY NBS PLUS stent-grafts (Vascutek Terumo-Bolton Medical, Vascutek Germany GmbH, Hamburg, Germany) were released coated with a mixture of 40 ml SniPha 360 and 15.8% hydroxyethylcellulose gel. Afterwards the externally bacteriophage-coated grafts were re-assembled for endovascular placement. This was performed via the left common femoral artery. After overview angiography the two grafts were placed with small overlapping of the infected stent-graft. FIG. 18, FIG.

All invasive procedures were uneventful and no side effects were observed. After the endovascular treatment the patient was referred to a regular ward and recovered soon. Infection parameters decreased, the antibiotical medication was discontinued and the patient recovered. The signs of vasculitis disappeared as well. After four weeks of prolonged physio-therapeutical mobilization in hospital, the patient was discharged to follow-up rehabilitation therapy in good general condition.

A PET-CT scan performed three months after the bacteriophage treatment did not reveal signs of infection in or around the thoracic aorta were detected. The patient recovered further while infection parameters were undetectable. FIG. 20

DISCUSSION

This case demonstrates a successful treatment of an infected endovascular stent graft by means of local bacteriophage treatment. To our knowledge, this is the first time a stent-graft was impregnated with bacteriophages for local endovascular application.

Bacteriophages are known as a potent anti-bacterial treatment due to their lytic activity. Compared to other antibacterial therapeutic strategies like local Rifampicin treatment, bacteriophages have no cytotoxic effects on vascular cells[1]. In turn, they have the advantage that they act both on multi-drug resistant bacteria as well as biofilm-organized bacteria. Recently, a case series of eight patients with infections of vascular grafts, surgical wounds or implanted medical devices further demonstrated the feasibility of using different bacteriophages with lytic activity for successful treatment of bacterial infections[2]. Although bacteriophages were used for successful treatment of infections of vascular implants, bacteriophage treatment is still not common and no officially recommended option for infections in the Westernized hemisphere.

In present case, the physical condition and the significant comorbidities disqualified the patient for a surgical resection of the infected stent-graft and anatomical reconstruction of the thoracic aorta. By applying bacteriophages both into the vascular lumen as well as onto the peri-prosthetic tissues the graft infection with *Staphylococcus aureus* was successfully treated. The endovascular application of bacteriophages using a releasable stent-graft coated with bacteriophages and re-assembled under sterile conditions before it is insertion into the patient was an important issue of the approach. The intravascular application of phages intravascular directly to the infection site, thus assured a maximum concentration, contact time and invasion of the bacteriophages into the infected tissue.

Although multiple operative steps, including two times thoracotomy and the endovascular stent graft application, were performed, the respective distress caused by each procedure was markedly less compared to classical surgical treatment. The prolonged postoperative period at the hospital was due to the already initially weak condition of the patient, which required an extensive physiotherapeutical mobilization.

Since the physical condition of the patient significantly improved over the time and a three month follow-up PET-CT scan revealed no signs of infections, it could be assumed that the bacteriophage treatment was successful. However, there is an ongoing follow-up for the patient to assure a lasting treatment success.

In summary, this case report demonstrates that bacteriophage treatment could be a curative treatment option for patients that are not suitable for extensive surgical approaches. It is of particular importance that this success was only possible due to the hydrogel comprising HEC and bacteriophages according to the first aspect of the present invention, which allowed localization of phages in situ at the site of infection as well as continuous bacteriophage release in a retarded manner.

EXAMPLE 3

Successful Treatment of a Chronically Infected and Occluded Aorto-Bifemoral Dacron® Bypass with Bacteriophages Objectives:

Graft infections are severe and dreaded complications in vascular surgery. The surgical resection of infected aortic grafts is associated with high mortality and morbidity. Therefore, alternatives to inadequate antibiotic treatment and extensive surgery are indispensable.

Case:

A 66 year-old patient was admitted with an infection of a chronically occluded aorto-bifemoral Dacron® prosthetic bypass. After various transfemoral surgical recanalization attempts in the anamnesis, there were hostile tissue conditions on both femoral sides with chronic wound infection and exposed grafts. Local infection was confirmed by PET-CT imaging. Due to the patient's comorbidities, nothing but the sole explanation of the prosthetic bypass was medically indicated and reasonable. Further we intended to treat the bilateral femoral wound healing disorder. Bacteriophages were contemplated to be an alternative therapy option for intra- and postoperative therapy of the graft related soft tissue infection. After relaparotomy, the infected aortic prosthesis was extirpated, and the aorta was sutured. Bacteriophage suspension was instilled on a Tabotamb-Snow®, which was then placed retroperitoneally. After the femoral anastomoses had been discontinued, a bacteriophage-soaked fleece was placed bilaterally on the femoral side, using the same principle. The wounds were mobilized and closed without further drainage. After 10 days of inpatient stay, the patient could be discharged with subjective well-being, irritation-free wound conditions and without systemic inflammation parameters. PET-CT imaging at three months post intervention did not show signs of infection around the aorta or both femoral regions.

SUMMARY

This case demonstrates the supportive antibacterial effect of bacteriophages in septic aortic surgery and the successful secondary closure of chronically infected femoral wounds in high-risk patients. Above all, it demonstrates the superior efficiency of the hydrogel comprising HEC and bacteriophages according to the first aspect of the present invention, which allowed localization of phages in situ at the site of infection as well as continuous bacteriophage release in a retarded manner.

BACKGROUND

In vascular surgery, infections of the vascular grafts are considered to be severe complications. Especially infections of aortic grafts are associated with a high morbidity and mortality of up to 75%. Since these procedures are often performed in patients with multiple comorbidities, the required explantation of the infected graft and the extensive struggle with the related abdominal infection is related with an early postoperative morbidity and mortality of even over 20%. Despite the initial achievement of a successful treatment, the general rate of reinfection can be up to 20% of cases. This is mainly due to bacterial colonies embedded in the peri-prosthetic tissue, which then form a surface-adherent biofilm and hence have an up to 1000-fold greater resistance to antibiotic administration. Even a targeted antibiosis appropriate to antimicrobial susceptibility testing can only suppress a graft infection but does not constitute a curative treatment option. The most common pathogenic bacteria associated with graft inflammation are *Staphylococcus aureus, Staphylococcus epidermidis* and other coagulase-negative staphylococci, Enterobacterales,

*Pseudomonas aeruginosa* and corynebacteria [3]. These bacteria regularly enhance their specific virulence by attaching to the prosthetic material, and hence averting the local immune response by forming biofilms, that hinder phagocytosis. Furthermore, systemic antibiotic therapy is often inadequate due to the lack of effective saturation concentrations within the inflammatory periprosthetic tissue. In order to reduce the morbidity and mortality associated with the often inevitable surgical treatment, less invasive approaches to adequately treat the infection of the surrounding tissue are urgently needed. In this context, bacteriophages and their bacteriolytic activity are a promising therapeutic option.

Case

In November 2020, a 66 year-old male patient was referred to the emergency ward by his general practitioner with the clinical symptom of an acute abdomen. The examination revealed ubiquitous tenderness on all quadrants with peritonism in the lower abdomen. An infection with SARS-CoV-2 was ruled out. Further examination showed an elevated body temperature of 39.2° C., and blood testing revealed a leukocyte count of $9.4\times10^9$/l, as well as an elevated serum C-reactive protein of 90.2 mg/l. The chest X-ray depicted no evidence of pneumonia. An endocarditis was ruled out. Calculated antibiotic therapy with ampicillin/sulbactam was started in the usual dosage intravenously. Blood cultures were positive for Methicillin-susceptible *Staphylococcus aureus*. Secondary findings included the status of ubiquitous arterial occlusive disease. Due to the necessity of numerous vascular operations on both legs, the patient had eventually undergone a thigh amputation on the right side 12 months earlier; the left side revealed a chronically occluded polytetrafluorethylene (PTFE) Stockmann bypass still in situ.

After various transfemoral surgical recanalization attempts in the anamnesis, there were hostile tissue conditions bifemoral with a chronic wound infection leading to exposed graft material. Wound swabs exposed the presence of *Staphylococcus aureus* and *Escherichia coli*, indicating a polymicrobial infection. The peripheral blood flow of the lower limbs was compensated. Initially, a CT scan of the abdomen was performed, whereupon an occluded and infected aorto-bifemoral graft was assumed. The subsequently performed PET-CT scan displayed a visibly increased metabolic activity in the area of the graft, so that we diagnosed a chronically occluded and infected aorto-bifemoral prosthetic bypass with subsequential bifemoral infections, leading to the cutaneous wound healing disorder. FIG. 21

Due to the patient's comorbidities, we generally intended an operation and anesthesia time as short as possible with an efficacious treatment by explanting the prosthetic bypass. Further we planned to forego a lavage program for the septic abdomen and intended a primary closure of the abdomen. In order to treat the local inflammation in the abdominal and femoral areas in the long term intra- and postoperatively, the use of bacteriophages was considered to be plausible alternative therapy option in this case. The patient himself favored an alternative solution compared to an indefinite lasting systemical antibacterial treatment. Therefore, an experimental approach using local bacteriophage application was intended as a last resort treatment in line with Article 37 of the Declaration of Helsinki and in unity with the local ethics committee (A 2021-0208).

Bacteriophage Treatment

As a curative therapeutic strategy an intra and extra abdominal application of SniPha 360 (Phage24.com, Austria) was executed. SniPha 360 is a commercially available bacteriophage cocktail of lytic bacteriophages against *Escherichia coli, Staphylococcus aureus, Pseudomonas aeruginosa, Streptococcus pyogenes, Proteus vulgaris* and *Proteus mirabilis*. After outlining the potential risks but also benefits of the experimental procedure, the patient consented to the therapy. When performing the relaparotomy, cloudy fluid appeared within the abdomen. After an initial lavage, the retroperitoneum was opened, and the proximal aorta was prepared for clamping. The aorto-bifemoral Dacron® prosthesis presented a shell of a biofilm and was embedded in putrid fluid. The infected aortic prosthesis was extirpated, and the aorta was then sutured over. The prosthesis was retrieved femorally after mobilization of the legs of the prosthesis. The bacteriophage suspension was instilled on Tabotamb-Snow®, which was placed retroperitoneally around the infection. The retroperitoneum and abdomen were primarily closed without further drainage. After removing the femoral anastomoses, the wound conditions were debrided, mobilized and lavaged with a sharp spoon. A bacteriophage-soaked fleece was then placed bilaterally on the femoral side by the same principle, and the wounds were closed again without further drainage.

The operation time was 52 minutes, without significant blood loss. Subsequently the patient could be taken to the intensive care unit and extubated without the need for catecholamines. After 10 days of hospitalization, the patient could be discharged with subjective well-being, irritation-free wound conditions and normal findings for inflammatory values in the blood. PET-CT imaging at three months post intervention did not show signs of infection enclosing the aorta or both femoral regions.

DISCUSSION

This case demonstrates a successful treatment of a chronically infected occluded aorto-bifemoral Dacron® bypass by a local bacteriophage application. Especially, it was demonstrated that this success was only possible due to the hydrogel comprising HEC and bacteriophages according to the first aspect of the present invention, which allowed localization of phages in situ at the site of infection as well as continuous bacteriophage release in a retarded manner.

It is assumed that around 50-65% of prosthesis infections are a result of bacterial contamination during surgery [3,4]. A general distinction is made between early (up to 30 days postoperatively) and late infections, although the classification is arbitrary [3,4]. Early prosthesis infections are often assumed to be a consequence of intraoperative contamination and late infections to be a result of hematogenous bacterial spread, but profound evidence for this is limited. Late infections are usually caused by insufficient tissue integration of the prosthesis into the graft bed. Common pathogenic agents are staphylococci, enterobacteria and corynebacteria [3,4]. Bacteriophages (or simply 'phages'; Greek: "bacteria eater") are viruses that selectively infect bacterial cells and were first described in 1917 by the Canadian Félix Hubert d'Hérelle.

Currently Bacteriophages are known as a potent antibacterial treatment due to their lytic activity. They are considerably stable when exposed to the inflammatory environment and contribute significantly to the regulation of global bacterial mass. A bacteriophage can only multiply where its host is. They are highly specific and therefore predominantly affect strains within one bacterial species, rarely crossing species boundaries [5].

In the first (lytic) cycle of viral reproduction, phages kill their corresponding bacteria through lysis: once infected, the bacterium host cell then starts the process of reproduction, the destruction of the bacterium, and the release of new phage particles; this process is controlled by enzymes and an interaction of bacterial and phage genes. In the second (lysogenic) cycle, the bacteriophage nucleic acid is integrated into the host bacterium's genome or forms a circular replicon in the bacterial cytoplasm. Compared to other antibacterial therapeutic strategies like local Rifampicin treatment, no cytotoxic effects on vascular cells could be found for bacteriophages.

In addition, they are effective on multi-drug resistant bacteria as well as biofilm-organized bacteria. Recently, in a case series of eight patients with infections of vascular grafts, surgical wounds or implanted medical devices further demonstrated the feasibility of using different bacteriophages with lytic activity for successful treatment of bacterial infections. Although bacteriophages were used for successful treatment of infections of vascular implants, bacteriophage treatment is still not common and not an officially recommended option for infections in the westernized hemisphere. The retro- and intraabdominal application of phages directly to the infection site ensured a maximum concentration, contact time and invasion of the bacteriophages into the infected peri graft tissue. We were able to perform a short operation time, a definite treatment in respect to complete skin/wound closure and the forego of any drainages. No bacteriophage related clinical adverse events had been detected in our case. A three-month follow-up PET-CT scan revealed no signs of infections. It could be assumed that the bacteriophage treatment was successful.

In order to treat the local inflammation in the abdominal and femoral areas in the long term intra- and postoperatively, we perceived the use of bacteriophages as an alternative therapy option in antibacterial local therapy. However, there is an ongoing follow-up for the patient to assure a lasting treatment success. In summary, this case report demonstrates that bacteriophage treatment could be a curative treatment option for patients with bacterial graft- and peri graft infections that are not suitable for extensive surgical approaches.

EXAMPLE 4

Testing Bacteriophages Activity in Lyophilizate

Methods

In order to test the activity of bacteriophages in lyophilizated hydrogel, five lyophilizates from phage gel (composition: HEC: 13 g=13%, $CaCl_2$-Solution: 43 g=43%, glycerol 85%: 27 g=27%, water: 17 g=17%) were prepared (see FIG. 25). Subsequently, the lyophilizated hydrogels were centered on an agar-agar plate set with *Staphylococcus aureus* (see FIG. 26) and incubated at 36° C. for 24 h.

Results

The freeze-dried hydrogel was shown to be degraded via the gel state and then diluted (here: mainly by water from the culture medium). The activity of the phages remained, which, was recognizable by the corresponding bacteria-free (circled) plaques on the culture medium (see FIG. 27).

EXAMPLE 5

Testing Phage Release Out of Lyophlizated Hydrogels

Methods

Preparation of Lyophilizates

Hydrogels B and C Used for Lyophilization have the Following Composition:

HEC: B=7 g=7%/C14 g=14%

CaCl2-Solution: 43 g=43%

Glycerol 85%: 27 g=27%

Water: B=10 g=23%/C=16 g=16%

These hydrogels comprising bacteriophages were prepared as sterile gels and lyophilization was performed in a sterile environment as well.

The Following Lyophilizated Products were Prepared and Tested as Described Below:

| | |
|---|---|
| 7 g Gel+3 ml BPh-Buffer*+4 ml Aqua ad inj.→>15×$10^{11}$ PFU/ml | B1 |
| 7 g Gel+6 ml BPh-Buffer*+1 ml Aqua ad inj.→>30×$10^{11}$ PFU/ml | B2 |
| 7 g Gel+3 ml BPh-Buffer*+4 ml Aqua ad inj.→>15×$10^{11}$ PFU/ml | C1 |
| 7 g Gel+6 ml BPh-Buffer*+1 ml Aqua ad inj.→>30×$10^{11}$ PFU/ml | C2 |

BPh-Buffer >5×$10^{11}$ PFU/ml

Bph-Buffer: Tris buffer comprising sodium chloride, magnesium chloride (×7H2O) and Tris-HCl, pH=7.4

Of the products B1, B2, C1 and C2, C1 and C2 are the most solid formulation due to the gel former content (double amount of HEC), whereby Variant 2 of B and C (B2 and C2) contains the double concentration of BPh.

Release Tests

First, the lyophillizated products B1, B2, C1 and C2 were each released in 100 ml of sterile, physiological NaCl solution (0.9%) over 2 h. Thereby, NaCl solution was used, which was previously sterilized by sterile filtration. Further used utensils, such as bottles, stirring fish, etc., were sterilized by prior via steam sterilization.

Over the next 2 hours, samples were drawn by extracting 1 ml every 15 min, whereby the sample volume was not replaced. If necessary, a sample was diluted. Subsequently, samples were distributed on set *Staphylococcus aureus* plates and incubated for 24 h at 37° C. In total, 2 runs per gel variant were performed (n=2).

Results Release Tests

To sum up, the results showed that there is a strongly retarded release of phages from freeze-dried hydrogels (see FIG. 29).

Moreover, the curves show that a higher proportion of gel former (C1 and C2) shows stronger retarded release in comparison to a lower proportion of gel former (B1 and B2). Further, a lower phage conc. (pfu/ml) in the starting gel (B1, C1) consequently also showed a lower phage release per time in comparison to a higher phage concentration (B2, C2) in the starting gel.

EXAMPLE 6

Therapy of Acne Inversa Using a Bacteriophage Cocktail in Connection with a Galenic Carrier in a Clinical Comparison to the Gold Standard Abstract:

Acne inversa is a chronic skin disease. Painful inflammation develops in the area of the hair follicles. As a result, abscesses, fistulas and nodular scarring can develop. The inflammation occurs mainly in the armpits and in the groin, anal and genital regions. In the present treatment attempt, findings in the left axilla were applied in accordance with a treatment attempt according to § 37 of the Helsinki Declaration with a hydrogel comprising HEC and bacteriophages, while a clinically similar finding on the right gluteal side was treated conventionally with open wound treatment.

In the short and long term, there are clear clinical advantages with regard to bacteriophage therapy.

Introduction

The patient was presented with the referral of the family doctor with suspected acne inversa at several locations, especially left axillary and right gluteal (Hurley stage II/III). The patient had already had an axillary operation in 1997 and a posterior operation on the thighs in 2011 due to acne inversa.

Since last year there has been a continuous deterioration under drug therapy with adalimub (Hyrimoz) 40 mg and cefpodoxime 200 mg and local Fucidin. The patient was in severe pain and could hardly sit, right arm rotation was painful and restricted movement. Intermittent fever was mentioned. Associated diseases are arterial hypertension, a factor V Leiden mutation, the Z.n. Pulmonary artery embolism in 1996, 1998, 2003 and nicotine abuse.

Findings on inpatient admission—in the axillary, inguinal and, above all, the gluteal area on the right, there—were inflammatory nodules that were tender to pressure, furthermore abscesses, fistula and scar formation, equivalent to Hurley stage II/III (see FIG. 31). In the laboratory blood there was a leukocytosis with WBC 21×10 high 9/l and a CRP of 30 mg/l (3 mg/dl). Wound swabs were not taken.

Methods:

Admission was initiated for surgical care and in connection with planned bacteriophage injection as a healing attempt according to § 37 Helsinki Declaration. A local anaesthesia was performed with 20 ml Scandicain 1% subcutaneously in the aera of surgical axillary access (see FIG. 31, top left). After en-bloc resection via two separate accesses to the infected soft tissue, the wound surface was injected subcutaneously with 20 ml of a bacteriophage galenic in a viscous state (see FIG. 31, top right and bottom left) comprising phage cocktail SniPha 360 from the company Phage 24® with a phage concentration of at least $1\times10^5$ against the germs *S. aureus, Streptococcus pyogenes, E. coli, P. aeroginosa, Proteus vulgaris* and *Proteus* smirabilis (composition of galenic: HEC: 13 g=13%, $CaCl_2$-Solution: 43 g=43%, glycerol 85%: 27 g=27%, water: 17 g=17%). The skin was then mobilized and primarily closed without further drainage (see FIG. 31, bottom right). In the course of the inpatient treatment, only dry dressings were changed. The sutures were removed 12 days post OR.

In contrast to this, general anaesthesia needed to be performed because of persisting pain under local anaesthesia. In this topic, open excision and open wound treatment were chosen as the gold standard therapy for acne inversa on the right gluteal side. The intraoperatively adapted VAC pump was checked regularly and could be removed after 5 days. The wound was showered daily afterwards and was clean and free of irritation before discharge. The further procedure was daily cleaning with Octenisept solution and douching of the wound as well as a moist wound dressing until the wound had completely granulated Results:

The patient presented to the clinic 2 weeks and 10 weeks after the surgical intervention for clinical follow-up. The right axillary wound was continuously clean and dry with a 1 mm large, clearly exuding pore in the middle of the larger access wound (see FIG. 32, left), which was closed without irritation 10 weeks after the operation (see FIG. 32, right). In the first wound check after 2 weeks, the gluteal wound was granulating but covered with fibrin (see FIG. 33, top). With continued wound treatment, a scarred, granulating wound was established 10 weeks after the operation (see FIG. 33, bottom).

Discussion

Acne inversa is a painful, chronic inflammatory skin condition that primarily affects the armpits, groin, pubic area and anus. The disease often begins with hair root inflammation and then spreads in the form of recurring inflammation and abscesses. An estimated 1% of the population is affected. A large number of bacteria can be found in acne inversa/hidradenitis suppurativa lesions, in particular *Staphylococcus aureus*. The disease is often diagnosed too late and at an advanced stage. Those affected often withdraw out of fear and shame, which can disrupt their professional career, personal and social relationships and lead to depression.

Depending on the severity, divided into Hurley grades I to Ill, those affected suffer from recurring pus the weeping wounds. Individual inflammatory nodules or abscesses in surrounding healthy tissue are usually found in patients classified as Hurley grade I. In grade II, progressive, defined inflammation with scarring and fistula formation is described. In grade Ill, there are extensive, interconnected abscesses and fistula tracts.

Hurley I: Local or systemic administration of antibiotics, if necessary surgical removal of individual lesions injuries/areas Hurley II: Systemic administration of antibiotics, administration of antibodies, surgical removal of individual injuries, if necessary removal of superficial tissue layers using a laser Hurley III: Systemic antibiotics, administration of antibodies, radical surgical removal of the affected tissue For wound treatment after an operation in Hurley grade II-III, according to the guideline therapy, it is recommended not to sew up the wound, but to let it heal "openly". Suitable wound dressings and, if necessary, negative pressure wound therapy (NPWT) are used to cover the "open" wound.

The present example impressively showed the potency of bacteriophage application in direct comparison to conventional treatment methods. Both the early inpatient and the postoperative course were unremarkable in relation to the axilla treated with bacteriophages, while in the area of the gluteal wound a complex, lengthy and cosmetically poor healing process could be documented.

The success of using the bacteriophage cocktail without prior sensitivity testing as part of a phagogram could be attributed to the use of different phages. The use of several bacteriophage increased the sensitivity rate and also targeted mixed infections. The subcutaneous application of standardized bacteriophage solution in connection with a carrier increased the topical residence time and the local bacteriophage concentration in the initial phase of infection treatment. A gel galenic was used as an application medium in addition to the bacteriophage solution in order to prevent the bacteriophage solution from running off the targeted area quickly. In this respect, the described gel galenics act like a reservoir for the phages. The application of a liquid solution is considered to be less effective, since the bacteriophage concentration cannot be optimally maintained topically.

The bacteriophage application in form of a hydrogel according to the present invention has proven to be a patient-friendly, inexpensive, side effect-free and fast therapy approach with excellent results in the present treatment trial. From a medical economic point of view, advantages for the bacteriophage application can be seen due to the clearly different healing processes.

Summary:

In the present case report, the application of a bacteriophage cocktail with a galenically defined carrier, which together form of a hydrogel according to the present invention, is superior to the conventional treatment of acne inversa type II/IIII according to Hurley.

EXAMPLE 7

Comparison of wound healing of wounds caused by subcutaneous bacterial infection in mice treated with various forms of bacteriophage-containing hydrogel Introduction Subcutaneous injection of *Staphylococcus aureus* in healthy mice generally leads to a bacterial infection causing open wounds. The reduction of bacterial burden is hence mandatory for a healing of the wounds as bacterial infection cause and expand skin destruction. Especially, wounds usually close faster when less bacteria are present. In the course of the infection, healing of these wounds supported by treatment with a hydrogel according to the present invention leads to wound seize reduction until upon complete healing, the wounds are entirely closed.

Consequently, wound seize reduction is an indirect indication for the effect of the respective treatment. The time, and hence the trend of how fast the wounds reduce over the time is an indirect but solid scientific read out for the used mice model.

Description:

In a mice model 5 groups of mice with 22 mice per group were tested. On day one all mice have been infected subcutaneously with the same amount of Staph. *Aureus*.

Therefore, 100 µL of bacterial suspension containing an appropriate number of colony forming units (CFU) was injected subcutaneously into the shaved area under ketamine/xylazine anaesthesia.

On day 3 all mice showed wounds that were treated with:

| | | | |
|---|---|---|---|
| I | HEC in the composition described | n.a. | 0.5 ml/mouse |
| II | Phage-Solution | $10^5$ pfu/ml | 0.5 ml/mouse |
| III | Phage-Solution + HEC in the composition described 1:1 | $10^5$ pfu/ml | 1.0 ml/mouse |
| IV | Phage-Solution + HEC in the composition described 1:2 | $10^{2.5}$ pfu/ml | 1.0 ml/mouse |
| V | non treatment | n.a. | |

(HEC composition: HEC (Hydroxy-ethyl-cellulose): 13 g = 13%, $CaCl_2$-Solution*: 43 g = 43%, glycerol 85%: 27 g = 27%, water: 17 g = 17%)

Thereby, the phage-solution used is SniPha 360 Phages—Phage Solution, Sanubiom.

The formulation for groups III and IV was prepared as follows: adequate volume of the HEC in the composition described was placed in a first Omnifix Luer lock syringe, while a second Omnifix syringe was filled with the phage solution. The two syringes were connected with an Omnifix adapter and the phage solution was pushed in the carrier. The formulation was fully mixed by the pushing of the solution back and forth between two syringes through the connector at least ten times.

On the following days, the respective wound seizes were measured (based on length and width of each lesion), averaged and trended. For ratio evaluation, the slope of the phage solution group was taken as the comparison group so that the slope ratio=1. Test results have been considered up to day 10, because afterwards the immune system overlapped the healing effects of the respective products.

Results:

The results show a superiority of the gel-phage combinations:

| | line | slope | Slope ratio | |
|---|---|---|---|---|
| I | | −0.1145 | 1.5226 | HEC in the composition described |
| II | | −0.0752 | 1.0000 | Phage-Solution |
| III | | −0.1628 | 2.1649 | Phage-Solution + HEC-Composition 1:1 |
| IV | | −0.1845 | 2.4535 | Phage-Solution + HEC-Composition 1:2 |
| V | | −0.0796 | 1.0585 | non treatment |

This is particularly evident from group IV, which has the best overall slope and a 2.5 times better slope in trending compared to Group II. Although, it holds only half the phage concentration in comparison to Groups II and III. Hence, Group I is 1.5 times better and Group II is about 2 times better concerning the trend of wound seize reduction. The Group II is comparable with Group V, that was left untreated.

The previously described trending shows the superiority of the phage-gel combinations over the non-treatment group and the phage-solution group (Group II).

Many products are used for wound treatment, but not a HEC gel in the composition described. The test showed that HEC in the composition described not only adequately carried the phages at the site of application, adhered to it adhesively and released the phages in a correspondingly retarded manner. In addition, it was also beneficial to wound healing: the HEC gel alone, in the composition described, without phages (Group 1) reduced the wound area in the trending 1.5 times faster than the phage solution. This effect can be explained on the one hand by the water contained and the hydrophilic gel properties. In addition, the adhesive character of the HEC in the composition described here is also evident: due to the tissue-friendly composition, the wound moistened by the hydrogel healed better than the wounds of the mice in the phage solution group, also due to the physical shielding to the outside.

In Group II, the phage solution quickly ran off the wounds when it was applied to them. Even a covering with the appropriate wound covering could not prevent this or increase the probability of a phage-bacterium interaction. This is clearly shown by the comparable values of the phage solution group (Group II) and the non-treatment group (Group V).

Groups III and IV showed two to two and a half times the wound reduction rate compared to Group II (phage solution). Particularly noteworthy is Group IV, which carried only half the phage concentration compared to Groups II and III. The properties of the HEC in the described composition are most evident here. Due to the properties already explained, wound healing was accelerated. The continued release of phage increased the interaction of phage and bacterium.

The phage solution (Group II) and Group Ill were carried out with the same phage solution quantity, here only the difference in connection with the carrier became apparent: Group III was better (=faster) by more than double with regard to wound healing. Further, it was shown that the more the carrier is increased in the proportion, the more the retarding release is forced: Group IV showed the fastest wound healing rate in trending with a phage concentration of only $10^{2.5}$ pfu/ml.

As a result, with the HEC described in this composition, therapeutic success was shown with phage concentrations of $10^5$ pfu/ml (Group III) only, which was 2-fold superior to the phage solution (Group II).

REFERENCES TO EXAMPLE 2

1. Szilagyi D E, Smith R F, Elliott J P, Vrandecic M P (1972) Infection in arterial reconstruction with synthetic grafts. Ann Surg 176: 321-333.
2. ZUhlke H V, Harnoss B M, Lorenz E P (1994) Postoperative Infektionen in der Gefäßchirurgie. In: Septische Gefäßchirurgie Blackwell Wiss Verlag.

REFERENCES TO EXAMPLE 3

[3] Kirklin J K, Pagani F D, Kormos R L, Stevenson L W, Blume E D, Myers S L, et al. Eighth annual INTERMACS report: Special focus on framing the impact of adverse events. The Journal of Heart and Lung Transplantation 2017; 36:1080-6.
[4] Kim: J, Feller E D, Chen W, Liang Y, Dilsizian V. FDG PET/C T for Early Detection and Localization of Left Ventricular Assist Device Infection: Impact on Patient Management and Outcome. JACC Cardiovasc Imaging 2019; 12:722-9.
[5] Baddour L M, Wilson W R, Bayer A S, Fowler V G, Tleyjeh I M, Rybak M J, et al. Infective Endocarditis in Adults: Diagnosis, Antimicrobial Therapy, and Management of Complications: A Scientific Statement for Healthcare Professionals From the American Heart Association. Circulation 2015; 132:1435-86.

REFERENCES TO EXAMPLE 7

6—F. Altamirano, J. Barr—Phage Therapy in the Postantibiotic Era—Clin Microbiol Rev. 2019 Jan. 16; 32(2): e00066-18. doi: 10.1128/CMR.00066-18.
7—D. Malik, I. Sokolov, G. Vinner, F. o Mancuso, A Kirpichnikova—Formulation, stabilisation and encapsulation of bacteriophage for phage therapy. Adv Colloid Interface Sci. 2017 November; 249:100-133. doi: 10.1016/j.cis.2017.05.014. Epub 2017 May 14.
8—L. Kasman, J. Norris—Overcoming the Phage Replication Threshold: a Mathematical Model with Implications for Phage Therapy—Journal of Virology 2002 Vol. 76, No. 11, doi.org/10.1128/jvi.76.11.5557-5564.2002
9—E. Morello, L. Debarbieux—Pulmonary Bacteriophage Therapy on *Pseudomonas aeruginosa* Cystic Fibrosis Strains: First Steps Towards Treatment and Prevention—2011 plos on collection psychology, doi.org/10.1371/journal.pone.0016963
10—H. madavi, S. padmanabhan—Therapeutic Potential of Staphylococcal Bacteriophages for Nasal Decolonization of *Staphylococcus aureus* in Mice—Advances in Microbiology Vol. 3 No. 1(2013), Article ID:29179,9 pages DOI:10.4236/aim.2013.31008
11—D. Rhoads, A. Sulakvelidze—Bacteriophage therapy of venous leg ulcers in humans: results of a phase I safety trial—Journal of wound care 2013, Vol. 18, No. 6, doi.org/10.12968/jowc.2009.18.6.42801

The invention claimed is:

1. A hydrogel comprising hydroxyethyl cellulose (HEC), bacteriophages, 10% to 33% $CaCl_2$ and 11% to 22% glycerol.

2. The hydrogel of claim 1, wherein the hydrogel comprises 3% to 10% HEC.

3. The hydrogel of claim 1, wherein the concentration of the bacteriophages is from $10^2$ pfu/ml to $10^8$ pfu/ml.

4. The hydrogel of claim 1, comprising
$10^2$ pfu/ml to $10^8$ pfu/ml bacteriophages,
3 to 10% HEC,
10 to 33% $CaCl_2$, and
11 to 22% glycerol.

5. The hydrogel of claim 1, further comprising a buffer.

6. The hydrogel of claim 1, wherein the hydrogel has a pH of 7.0 to 7.8.

7. The hydrogel of claim 1, wherein the hydrogel has a viscosity of 1000 mPas up to 100,000 mPas.

8. The hydrogel of claim 1, comprising
$10^2$ pfu/ml to $10^8$ pfu/ml bacteriophages,
3 to 10% HEC,
15 to 30% $CaCl_2$, and
12 to 20% glycerol.

9. The hydrogel of claim 1, comprising
$10^2$ pfu/ml to $10^8$ pfu/ml bacteriophages,
3 to 10% HEC,
17 to 23% $CaCl_2$, and
12 to 15% glycerol.

10. A lyophilizate of the hydrogel of claim 1.

11. A method of preparing a hydrogel comprising hydroxyethyl cellulose (HEC) and bacteriophages comprising the steps of
a) providing HEC in a solid state of matter,
b) dissolving solid HEC of step a) in a liquid component comprising water and bacteriophages, and
c) optionally adding water until the desired viscosity is reached.

12. A method of treating and/or preventing a bacterial infection in a subject in need thereof, comprising administering to the subject and effective amount of the hydrogel or a lyophilizate of the hydrogel of claim 1.

13. The method of claim 12, wherein the subject has been identified as suffering from a bacterial infection and the hydrogel or the lyophilizate is administered to the identified subject.

14. The method of claim 12, wherein the hydrogel or the lyophilizate of the hydrogel is applied to the subject during surgery of the subject.

15. The method of claim 12, wherein the hydrogel or the lyophilizate of the hydrogel is applied to a surgical site, an implant, an anastomosis, a wound, an abrasion, a cut, a stab, a non-intact skin tissue and/or mucosal tissue, an entrance point of a catheter, a covering of sterile material, a wound and/or implant coverage, and/or suture material.

16. The method of claim 12, wherein the hydrogel or the lyophilizate of the hydrogel is used to treat and-/-or prevent a bacterial infection associated with an implant.

17. The method of claim 12, wherein the hydrogel or the lyophilizate of the hydrogel is directly applied to a surface of the implant, either outside of a subject's body or in a subject's body.

18. The method of claim 12, wherein the hydrogel or the lyophilizate of the hydrogel is applied to a surface of a subject's body or to a surface of an implant manually and/or using one or more helping devices.

19. The method of claim 18, wherein the one or more helping devices are selected from syringes, needles and catheters.

20. The method of claim 12 wherein the subject is a human.

* * * * *